(12) United States Patent
Jauernig et al.

(10) Patent No.: US 7,758,886 B2
(45) Date of Patent: Jul. 20, 2010

(54) PHARMACEUTICAL AEROSOL COMPOSITION

(75) Inventors: Jurgen Jauernig, Penzberg (DE); Frank-Christophe Lintz, Starnberg (DE); Manfred Keller, München (DE); Ingo Friedrich, München (DE)

(73) Assignee: Pari GmbH, Starnberg (DE)

( * ) Notice: Subject to any disclaimer, the term of this patent is extended or adjusted under 35 U.S.C. 154(b) by 127 days.

(21) Appl. No.: 11/106,999

(22) Filed: Apr. 14, 2005

(65) Prior Publication Data

US 2005/0244339 A1    Nov. 3, 2005

Related U.S. Application Data

(63) Continuation-in-part of application No. PCT/EP2004/011571, filed on Oct. 14, 2004.

(30) Foreign Application Priority Data

Oct. 15, 2003    (DE)    ................ 103 47 994

(51) Int. Cl.
  *A61K 9/12*    (2006.01)
  *A61K 9/127*   (2006.01)
  *A61K 9/133*   (2006.01)
(52) U.S. Cl. .................. 424/450; 424/45; 424/434; 264/4.1
(58) Field of Classification Search ................ 424/450, 424/45, 434; 264/4.1
See application file for complete search history.

(56) References Cited

U.S. PATENT DOCUMENTS

| | | | |
|---|---|---|---|
| 4,125,186 A | | 11/1978 | Meierhoefer |
| 4,150,071 A | | 4/1979 | Pecina |
| 5,006,343 A | * | 4/1991 | Benson et al. ............... 424/450 |
| 5,192,528 A | * | 3/1993 | Radhakrishnan et al. ...... 424/45 |
| 5,336,507 A | | 8/1994 | Na et al. |
| 5,364,632 A | | 11/1994 | Benita et al. |
| 5,470,583 A | | 11/1995 | Na et al. |
| 6,086,376 A | | 7/2000 | Moussa et al. |
| 6,241,969 B1 | * | 6/2001 | Saidi et al. .................... 424/45 |
| 6,465,016 B2 | * | 10/2002 | Parikh et al. ................. 424/489 |
| 6,660,286 B1 | * | 12/2003 | Lambert et al. .............. 424/405 |
| 6,890,517 B2 | * | 5/2005 | Drechsel et al. ............... 424/45 |
| 2002/0013271 A1 | | 1/2002 | Parikh et al. |
| 2003/0055026 A1 | | 3/2003 | Banerjee et al. |
| 2003/0073676 A1 | | 4/2003 | Biggadike et al. |
| 2003/0129242 A1 | | 7/2003 | Bosch et al. |
| 2005/0244339 A1 | | 11/2005 | Jauernig et al. |

FOREIGN PATENT DOCUMENTS

| | | |
|---|---|---|
| DE | 4203306 A1 | 8/1993 |
| DE | 697 27 849 T2 | 10/2001 |
| DE | 101 45 361 A1 | 4/2003 |
| DE | 695 23 587 T2 | 3/2004 |
| DE | 102 39 321 B3 | 4/2004 |
| EP | 0 694 314 A1 | 1/1996 |
| EP | 0 729 764 A1 | 9/1996 |
| EP | 0 760 649 B1 | 10/2001 |
| EP | 0 799 620 B1 | 3/2004 |
| RU | 2 180 217 | 3/2002 |
| WO | WO-96/13254 | 5/1996 |
| WO | WO-97/29738 | 8/1997 |
| WO | WO-97/42938 | 11/1997 |
| WO | WO-00/27376 | 5/2000 |
| WO | WO-01/78743 A1 | 10/2001 |
| WO | WO-01/78744 A1 | 10/2001 |
| WO | WO-01/78745 A1 | 10/2001 |
| WO | WO-03/035030 A1 | 5/2003 |
| WO | WO-2004/019985 A1 | 3/2004 |
| WO | WO-2004/020029 A1 | 3/2004 |
| WO | WO-2005/037246 A2 | 4/2005 |

OTHER PUBLICATIONS

Klyashchisky et al, Nebulizer-compatible liquid formulations for aerosol pulmonary delivery of hydrophobic drugs: Glucocorticosteroids and Cyclosporine, Journal of drug testing, 1999, vol. 7, No. 2, pp. 79-99.*

M. Keller, "Development and Trends in Pulmonary Drug Delivery," Chimica Oggi, Chemistry Today, No. 11/12, 1998.

N. Luangkhot et al., "Characterization of salbutamol solution compared to budesonide suspensions consisting of submicron and micrometer particles in the PARI LC Star® and a new PARI Electronic Nebuliser (e-Flow)," Drug Delivery to the Lungs XI, Dec. 11-12, 2000, pp. 14-17.

M. Keller et al., "Nebulizer Nanosuspensions: Important Device and Formulation Interactions," Resp. Drug Delivery VIII, 2002, pp. 197-206.

A. Vaghi et al., "In vitro comparison of Pulmicort Respules™ with Clenil™ per aerosol in combination with three nebulisers," ERS, Annual Congress Stockholm, Sep. 14-18, 2002.

M. Keller et al., "Using Infant Deposition Models to Improve Inhaler System Design," Resp. Drug Delivery IX, 2004, pp. 221-231.

A. Weber et al., "Effect of Nebulizer Type and Antibiotic Concentration on Device Performance," Pediatric Pulmonology (1997), 23, 249-260.

(Continued)

*Primary Examiner*—Mina Haghighatian
(74) *Attorney, Agent, or Firm*—Peter F. Corless; Christine C. O'Day; Edwards Angell Palmer & Dodge LLP

(57) ABSTRACT

Sterile compositions for administration as aerosols are described. They contain an active agent which is poorly water-soluble, a non-ionic surfactant acomponent and a phospholipid component. The compositions are suitable for oral or nasal inhalation, but also for topical or oromucosal administration. They are particulary useful for the efficient pulmonary administration of poorly soluble corticosteroids and can be aerosolized with common nebulizers.

51 Claims, 1 Drawing Sheet

OTHER PUBLICATIONS

R. Hughes et al., "Use of isotonic nebulised magnesium sulphate as an adjuvant to salbutamol in treatment of severe asthma in adults: randomised placebo-controlled trial," Lancet, 2003; 361 (9375): 2114-7.

H. Stricker, "Kolloidale and makromolekulare disperse Systeme," *Physikalische Pharmazie*, 3rd edition, p. 440 (1987), with English translation of the table.

S. Vemuri et al., "Preparation and characterization of liposomes as therapeutic delivery systems: a review," Pharm. Acta Helv. 1995, 70(2):95-111.

A. Coates et al., "Accounting for Radioactivity before and after Nebulization of Tobramycin to Insure Accuracy of Quantification of Lung Deposition," Journal of Aerosol Medicine (2000). vol. 13, No. 3, 169-178.

* cited by examiner

PHARMACEUTICAL AEROSOL COMPOSITION

The present application is a Continuation-in-Part of International Application No. PCT/EP2004/011571, filed Oct. 14, 2004, which in turn claimed the prior benefit of German Patent Application No. DE 103 47 994.5, filed Oct. 15, 2003.

TECHNICAL FIELD OF THE INVENTION

The invention relates to compositions which are useful as medicaments, or components of medicaments, for inhalation in aerosol form. The compositions contain an active agent and can be used pharmaceutically or to promote general well-being. In particular, the invention relates to sterile aqueous preparations for inhalation using a pump spray, a nebulizer, such as a jet, ultrasonic, or vibrating membrane nebulizer, or another aerosol generation system suitable for aqueous liquids. It further relates to the nasal or pulmonary administration of physicochemically, organoleptically or physiologically problematic active agents. According to further embodiments, the invention relates to methods for the manufacture of such compositions and their uses.

BACKGROUND OF THE INVENTION

The treatment of lung diseases by means of aerosols allows a targeted pharmaceutical therapy because the active agent can be delivered directly to the pharmacological target site by means of inhalation devices [D. Köhler and W. Fleischer: Theorie und Praxis der Inhalationstherapie, Arcis Verlag GmbH, München, 2000, ISBN 3-89075-140-7]. This requires that the inhaled droplets or particles reach the target tissue and are deposited there. The smaller the diameter of the aerosol particles, the greater is the probability that active agents reach the peripheral parts of the lungs. Depending on the kind and extent of the deposition, diseases such as asthma, chronic obstructive pulmonary disease (COPD) or pulmonary emphysema can be treated quasi-topically by inhalation. Moreover, systemically active agents such as insulin can be administered to the lung and taken up into the blood circulation by predominantly alveolar absorption. At present, mainly pressurized gas propelled metered dose inhalers, powder inhalers and nebulizers are used for the administration of active agents by inhalation. The type and extent of deposition at the target site depends on the droplet or particle size, the anatomy of the respiratory tract of humans or animals and on the breathing pattern. For the deposition of aerosols in the lungs of rodents such as rats, much smaller droplets are required than, for example, for horses, due to the smaller dimensions of the respiratory tract.

For pulmonary deposition in adults, aerosol droplets or particles should have an aerodynamic diameter of less than 5-6 µm, and for infants less than 2-3 µm. Moreover, infants breath through the nose, which is why nebulizing systems with a nasal mask should be used for the administration of active agents by inhalation. This restriction also applies in the case of other species such as rodents. The influences on the aerosol generation and deposition are mainly influenced by 3 factors which can be categorized as follows:

(1) bio-physiological factors, which are characterized by:
   the kind of the breathing maneuver such as breathing frequency, flow, rate and volume,
   the anatomy of the respiratory tract, in particular the glottal region,
   the age and the state of health of the patient;

(2) the droplet or particle spectrum, which is, in turn, influenced by:
   the kind and construction of the inhalation device,
   the time interval between generation and inhalation (drying properties),
   the modification of the droplet or particle spectrum by the respiratory flow,
   the stability or integrity of the generated aerosol cloud;

(3) the active agent or active agent preparation, whose properties are influenced by:
   the particle size,
   the dosage form (for example, solution, suspension, emulsion, liposome dispersion),
   the shape and surface properties of the active agent particles or the carrier particles (smooth spheres or folded porous structures) in the case of powder aerosols,
   the hygroscopicity (influences the growth of the particles),
   the interfacial properties such as wettability and spreadability,
   the evaporation properties of the carrier medium.

The advantages and disadvantages of the various inhalation devices and the possibilities to compensate inherent disadvantages have been discussed by M. Keller [Development and Trends in Pulmonary Drug Delivery, Chimica Oggi, Chemistry today, No. 11/12, 1998].

The question where aerosol particles are deposited in the bronchial tree has been the subject of numerous investigations for several years. These investigations are supplemented by constantly improving computational models of pulmonary deposition. The regional deposition pattern in breathing through the mouth shows a high degree of variability due to the breathing maneuver and the varying anatomy of the bronchial tree. The respirable size range of 0.5-6 µm, which is frequently mentioned in the literature, does not take into account the overlapping regions of deposition nor the quantitative or relative deposition rates.

In a healthy adult breathing through the mouth about 40-60% of the particles in the range of 2.5-4.5 µm are preferably deposited in the alveolar region. A bronchial deposition of the order of magnitude of about 5-28% is exhibited for particles of 2 to 8 µm, while the oropharyngeal deposition increases in parallel. For particles of 6 µm, the deposition in the oropharynx already amounts to 25-45% and increases to 60-80% for particles with a diameter of 10 µm. It follows from this that, for an optimal qualitative and quantitative alveolar deposition in adult, particle sizes of 1.5-3 µm are advantageous if the oropharyngeal and bronchial deposition is to be as low as possible. The bronchial deposition of about 18-28% for particles in the size range of 6-9 µm is relatively low and is always accompanied by a correspondingly higher oropharyngeal deposition. Depending on the state of health, the geometry of the bronchial system and the age of the patient, the orders of magnitude stated above shift to smaller particles sizes, in particular in children and babies. In the case of infants of less than 1 year of age, it is assumed that only droplets or particles with an aerodynamic diameter less than 2-3 µm reach the deeper regions of the lungs to a significant extent.

For the treatment of sinusitis it is also known that only the smallest aerosol droplets reach the sinuses through the small ostio openings such that more active agent can be deposited at the target site by means of a pulse aerosol than with continuous nebulization.

The deposition of aerosol particles in the respiratory act is essentially determined by the following four parameters:
   the particle size,
   the particle velocity, the geometry of the respiratory tract, and
the inhalation technique or breathing maneuver.

It can be derived from Stokes' law that the flow velocity and density of aerosol particles are relevant, which is why the aerodynamic and not the geometric particle diameter is used as the quantity to be measured for the deposition behavior in the respiratory tract. It is known from various investigations that only droplet or particle sizes with an aerodynamic diameter of about 0.6 µm-6 µm can be employed for pulmonary therapy. Particles with an aerodynamic diameter of greater than about 6 µm impact in the upper respiratory tract, whereas those which are smaller than about 1 µm are exhaled after inhalation. This implies that, for example, powders with very low density and an aerodynamic diameter of about 3 µm can have a geometric diameter of, for example, greater than 10 µm. In aqueous systems, on the contrary, with density of about 1 mg/cm3, the geometric and aerodynamic diameters are approximately equal.

The droplet compositions and form of aerosols are very diverse. Depending on the composition, aerosols may have a short or long life time; their droplet or particle size is subject to changes, which is influenced by the physical-chemical properties of the formulation components. Depending on atmospheric humidity, small aqueous droplets evaporate quickly to give a solid nucleus so that the concentration of the dissolved substance(es) upon complete evaporation is 100%. The resulting diameter ($d_2$), starting from the original diameter ($d_1$) corresponds to the cubic root of the concentration ratio before ($c_1$) and after ($c_2$) shrinkage (assuming a density of 1 g/cm$^3$ for the dissolved substance) according to the formula: $d_2 = d_1 \sqrt[3]{(c_1/c_2)}$. Thus, for example, the drying of aerosols formed by coastal waves by the wind, in the case of a seawater droplet ($c_1$=3.6%) of 20 µm, results in a salt particle with a diameter of about 6.7 µm, which has, thus, become respirable. This effect is employed, for example, in liquid nebulizers in order to reduce the particle size through drying effects (for example, heating by means of PARI Therm) or admixing of dry air.

On the contrary, in a humid environment, particles can grow and this growth is particularly dependent on the hygroscopicity of the active and/or auxiliary agent. For example, a dry sodium chloride particle of 0.5 µm requires about 1 second for complete growth, whereas in the case of a 5 µm particle this takes about 10 seconds, which proves that the velocity with respect to particle growth is also size dependent. Solid particles from powder nebulizers and metered dose inhalers can grow up to 4-5 times of their initial size since the humidity in the bronchial tree is 95-100%. (D. Köhler and W. Fleischer: Theorie und Praxis der Inhalationstherapie, Arcis Verlag GmbH, München 2000, ISBN 3-89075-140-7.)

For toxicological investigations, rodents and dogs are frequently used. Like infants, rodents breath through the nose, which is why in this case the aerosol should be applied by means of a nasal mask in order to achieve a high pulmonary deposition.

For the treatment of some pulmonary diseases such as asthma one mainly uses corticosteroids, beta-agonists and anticholinergic agents which are transported directly to the site of action by means of metered dose inhalers, powder inhalers and jet or ultrasonic nebulizers. The pulmonary application of corticosteroids for treatment of asthma has proven to be particularly advantageous compared to oral therapy because the underlying inflammatory process can effectively be inhibited with substantially lower active agent doses with marked reduction of adverse side effects. Active agents such as beclomethasone dipropionate (BDP), budesonide (Bud), and fluticasone propionate (FP) are mainly used as pump sprays for the treatment of allergic diseases in the nasal region, whereas metered dose inhalers (MDI), dry powder inhalers (DPI) and jet nebulizers are used for pulmonary application.

For the therapy of children under the age of 5 years powder inhalers are usually not suitable because children are not capable to generate flows of breath with which powders can reproducibly be de-agglomerated to give respirable particles and deposited in the lungs with sufficient dosage precision. Metered dose inhalers, on the other hand, have the disadvantage that the aerosol is released with a velocity of up to 100 km/h after operation of the valve. Due to insufficient coordination between the triggering of the spray pulse and inhalation, more than 90% of the active agent impact in the pharynx, which may result in unwanted side effect (hoarseness, voice changes, thrush, etc.). Moreover, the evaporation of the propellant gas can cause a cooling irritation, which, in hyperreactive patients can result in a de-generation of the epiglottis or in an asthmatic attack, for which reason the inhalation of steroids should always take place with so called spacers with a volume of about 250-750 ml. For the application of steroids in infants, who cannot breath through the mouth, there are special types of spacers (for example Babyhaler®) for nasal breathing. However, the use of MDIs and spacers is very complex because active agents sediment, adsorb to the spacer walls or become electrically charged. This can result in insufficient dosage precision and in a non-reproducible pharmaceutical therapy. This is the reason why the nebulization of aqueous preparations by means of jet, membrane or ultrasonic nebulizers for the pulmonary application of active agents in children and infants is advantageous compared to metered dose inhalers and powder inhalers if sufficiently small droplets or particles are generated.

The ideal situation for a therapy by means of nebulization of an aqueous preparation is a pharmaceutical substance which is sufficiently soluble and stable in water or isotonic saline solution and whose physical-chemical characteristics do not change during manufacture and storage. If, however, the solubility of the pharmaceutical substance is too low to prepare and aqueous solution of sufficient concentration, nebulization in the form of a suspension may be considered. By means of a breathing simulator various nebulization efficiencies (deposited dose, fraction of the pharmaceutical substance remaining in the nebulizer, etc.) can be detected for the selected pharmaceutical form (suspension or solution). The respirable fraction of the generated aerosol can be determined by measuring the relative proportion of the active agent containing droplets having a geometric or aerodynamic diameter of less than 5 or 3 µm by means of laser diffraction or impactor measurement [N. Luangkhot et al.; Characterization of salbutamol solution compared to budesonide suspensions consisting of submicron and micrometer particles in the PARI LC STAR and a new PARI Electronic Nebuiser (eFlow™). Drug Delivery to the Lungs XI, 11 & 12 Dec. 2000, p. 14-17].

In the aforementioned investigation, it is reported that budesonide-containing suspensions in which the particle size of the suspended pharmaceutical substance is markedly smaller than 1 µm, unlike a microsuspension, can be nebulized with an efficiency similar to that of a salbutamol sulfate solution. This finding is confirmed by Keller et al. [Nebulizer Nanosuspensions. Important device and formulation interactions, Resp. Drug Delivery VIII, 2002, p. 197-206]. Moreover, it is pointed out that microsuspensions should not be nebulized with an ultrasonic nebulizer. In a case of the nebulization of a budesonide suspension (Pulmicort®) it could be shown by ultra centrifugation that about 4.6% of the budesonide in Pulmicort® are dissolved or solublized in molecularly dispersed form and that only this fraction can be aerosolized by an ultrasonic nebulizer.

The aqueous corticosteroid preparations which are currently commercially available are microsuspensions of beclomethason dipropionate (Clenil®), budesonide (Pulmicort®) and fluticasone propionate (Flixotide®) i.e., the micronized active agent (about 90% of the suspended pharmaceutical substance particles are smaller than 5 µm) is present in finely dispersed and stabilized form in water. The smaller the particle size is of the active agent and the smaller the density difference between active agent and dispersing medium, the longer the active agent remains in the suspension, i.e., the slower sedimentation usually takes place. Before the application, the sedimented particles or agglomerates must be redispersed in fine form by shaking of the packaging means in order to ensure that as small an amount as possible of the active agent remains in the container and the nebulizer can be filled with the nominal dose. For this purpose and for improved wetting of the lipophilic active agent surface with water a surfactant or wetting agent is added, which, however, must be inhalation-toxicologically safe in order to avoid unwanted side effects. As an example, Pulmicort® shall be referred to, which is commercially available in three concentrations 0.25, 0.5 mg and 1 mg of budesonide per 2 ml. Budesonide is suspended in saline solution which is buffered with citric acid and sodium citrate and contains polysorbate 80 (=Tween® 80) as a wetting agent. The mean particle size of 3 tested lots of Pulmicort® was greater than specified (about 2.8-3.2 µm) and scattered between 3.7 and 4.4 µm. This differing finding may possible due to the method of measurement (laser diffraction), but may also be due to particle growth or particle agglomeration. In a publication by Vaghi et al. [In-vitro comparison of Pumicort Respules with Clenil® per aerosol in combination with three nebulizers, ERS, Annual Congress Stockholm, Sep. 14-18, 2002], electron-microscopic pictures of Pulmicort® and Clenil® were shown from which it follows that the particles in Clenil® are needle-shaped and mainly greater than 10 µm, whereas the Pulmicort® particles are more rounded and have a diameter in the range of about 1-6 µm. A further disadvantage is that the aerosol characteristics of such microsuspension can change during nebulization. This can be derived, for example, from the increase of the budesonide concentration in the residual non-nebulized Pulmicort® suspension. The explanation for this effect is, inter alia, that greater particles cannot be transported by aerosol droplets which have a smaller diameter and, therefore, remain as residue in the nebulizer. In membrane nebulizers, the course particles are retained by the sieving effect of the membrane generating the aerosol. From an economical point of view, this is disadvantageous.

In-vitro investigations using a Baby Cast SAINT Model (Sophia Anatomical Infant Nose Throat) have shown that, upon use of Pulmicort® and a jet nebulizer, only about 1% of the nominal amount of active agent could be detected as the pulmonary dose. [Using Infant Deposition Models To Improve Inhaler System Design. Resp. Drug Delivery IX, 2004, p. 221-231]. These findings are partly in accordance with clinical findings by pediatricians who report an insufficient efficacy of the Pulmicort® nebulization therapy in infants and find the explanation for this in that not enough active agent can be transported into the lungs because both the par-ticles and the droplets are too big for infants.

Therapy of the nasal mucosa appears to be somewhat simpler to handle. Here it is usually possible even with simple devices for aerosol generation, such as mechanical atomizers to sprinkle the mucosa with an active agent containing preparation. However, in this case, too, poorly soluble active agents represent a challenge. The efficacy of active agent suspensions employed in practice is rather low and poorly reliable in comparison to the amount of active agent used, which is probably due to the particularly slow dissolution of the active agent in the small liquid volumes which are available on the nasal mucosa.

On the contrary, therapy of the mucosa in the poorly ventilated cavities of the upper respiratory tract is particularly difficult even with easily handled active agents, and all the more so with poorly soluble active agents. Usually, only a very small fraction of the dose of a suspended active agent in aerosolized form reaches the target tissue.

STATE OF THE ART

There are a number of suggestions in the prior art as to how water insoluble active agents can be solubilized or dissolved. In particular, it has been attempted to prepare particulate systems with particle sizes in the nanometer range.

Document DE 101 45 361 A1 describes methods for the preparation of nano-particulate systems and a method for the preparation of a sterile submicron suspension. Although such submicron suspensions represent an improvement over conventional microsuspensions with particle diameters of about 1-6 µm for the reasons discussed above, they nevertheless have certain disadvantages because, even in the presence of a stabilizing wetting agent, particle growth due to "Ostwald Ripening" during storage cannot be entirely suppressed. Moreover, under certain storage conditions, dissolved particles may precipitate and, as it were, act as seeding crystals to promote particle growth. However, since particle size is of fundamental significance for therapeutic efficiency, products whose particle size cannot be kept constant during common pharmaceutical storage times of 2-3 years must be characterized as critical.

Document WO 00/27376 describes nano-particulate aqueous active agent preparations for the preparation of aerosols with the active agent particles exhibiting sizes of less than 1000 nm, preferably less than 50 nm. These preparations are prepared using surface modifying agents which adsorb to the surface of the active agent particles. Vitamin E-TPGS is proposed as one such agent.

Document RU 1280217 describes a mixture containing propylene glycol as solubilizing agent for the preparation of budesonide containing aqueous preparations. These preparations, however, have a high viscosity and are hyperosmolar, which is why a non-irritating treatment by inhalation is not possible, especially since the auxiliary agents used can presently not be characterized as inhalation-toxicologically safe. The use of propyleneglycol, even at a concentration from about 1%, gives hyperosmolar solutions which, upon inhalation, stimulate coughing. Moreover, they exhibit high viscosities, which is why formulations prepared using these auxiliary agents are less suitable for inhalation therapy and, on account of their physical properties alone, cannot be used with a vibrating membrane nebulizer.

In summary, it can be said that the problem of administration of poorly soluble active agents by aerosols for nasal or pulmonary application has so far not been solved satisfactorily. In particular the pulmonary administration of such substances to pediatric patients according to the state of the art is still extremely problematic.

Further types of active agents whose administration by inhalation is still not satisfactory are substances which patients consider irritating on account of their organoleptical properties, especially their bad taste or on account of their irritating effect on mucosa or the stimulation of coughing or bronchoconstriction, which may be an obstacle to sufficient compliance with a prescribed therapy and thus to therapeutic success.

Therefore, it is an object of the invention to provide improved preparations for the application as an aerosol which do not have the disadvantages of known preparations. In particular, it is an object of the invention to make it possible to administer by inhalation such active agents which, on account of their poor water solubility, their bad taste or their irritating effect on mucosa, could be administered by inhalation only in an unsatisfactory way. It is a further object of the invention to provide methods for the manufacture of such preparations utilizing standard sterile filtration (filters having pore sizes below 222 nm) which cannot be applied for suspensions containing particles above 220 nm. Other objects of the invention will become clear on the basis of the following description and the patent claims.

SUMMARY OF THE INVENTION

In a first aspect, the invention provides a sterile composition for administration as an aerosol which comprises a poorly water-soluble active agent which is not a surfactant; a non-ionic surfactant component, and a phospholipid component. Preferably, the poorly water-soluble active agent is an immunmodulator, such as cyclosporine or a corticosteroid such as budesonide, ciclesonide or fluticasone, or a derivative or combination thereof. The compositions may be solid, and designed to yield inhalable liquids upon combination with an aqueous liquid carrier. Alternative, they may be in aqueous liquid form.

In a further aspect, the invention provides medicaments which comprise a composition as described above as single or combination drug product. Such medicaments are useful in diagnosis, prophylaxis, and therapy. They are particularly useful for being nebulized with modern, highly efficient nebulizers, such as with devices comprising a vibrating membrane.

In another aspect, the invention provides methods for treating a human subject suffering from an inflammatory disease originating from the upper and lower respiratory tract including sinusitis, asthma, pediatric asthma, chronic obstructive bronchitis, bronchiectasis, lung emphysema, parenchymal and vascular lung disease, sarcosidosis, pulmonary and/or cystic fibrosis, pulmonary hypotension, lung cancer. The methods involve the repeated administration of a sterile aqueous composition which comprised a poorly water-soluble corticosteroid, a non-ionic surfactant component and a phospholipid component. The administration is achieved by nebulizing the composition by means of a nebulizer having a vibrating membrane with pores of; defined size. According to the method of the invention, the medicament is delivered from the nebulizer in aerosol form at a total output rate of about 0.2 to about 0.8 ml per minute, corresponding to about 200 to about 800 mg per minute.

It has been found that a combination of a non-ionic surfactant component and a phospholipid component in aqueous preparations, especially in connection with physiologically or physicochemically problematic active agents, can provide desirable pharmaceutical properties to an extent which is not to be expected from the knowledge of the mode of action of the individual surfactants; these pharmaceutical properties will be set forth in more detail below.

DETAILED DESCRIPTION OF THE INVENTION

Figure 1:
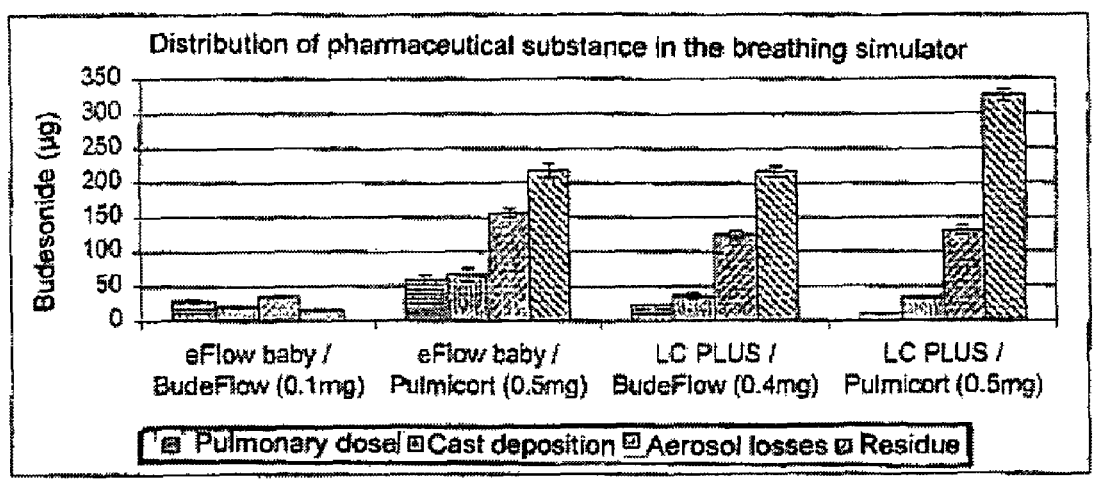
FIG. 1 shows a markedly improved pulmonary deposition for the colloidal budesonide solution (here referred to as "BUDeFlow®") in vitro using a respiratory tract model of a 9 months old baby (Sophia Anatomical Infant Nose Throat=SAINT Model) and lower unwanted nasal or oropharyngeal deposition than the Pulmicort® Suspension ("Pulmicort"), as is obvious from the relative ratio of the pulmonary dose to the "Cast Deposition".

According to a first aspect of the invention, a sterile composition is provided for administration as an aerosol, which comprises a poorly water-soluble active agent, a non-ionic surfactant component, and a phospholipid component. The active agent is not a surfactant.

It was surprisingly found by the inventors that poorly water-soluble active compounds could be solubilized to a substantial degree by incorporating both a non-ionic surfactant and a phospholipid component together with the active ingredient into compositions for inhalation, but also that the resulting compositions have further advantageous properties which make them particularly suitable for nebulization and improved inhalation therapies. For example, the compositions of the invention have a taste-masking potential for some active compounds having a poor taste, and they are stable and compatible with modern, highly efficient nebulizers, such as vibrating membrane devices.

As used herein, the term "sterility" is to be understood in the usual pharmaceutical sense. It is understood as the absence of germs which are capable of reproduction. Sterility is determined with suitable tests which are defined in the relevant pharmacopeias. According to current scientific standards, a sterility assurance level of $10^{-6}$ is generally regarded as acceptable for sterile preparations, i.e., one unit in a million might be contaminated.

In practice, however, contamination rates may be higher. For example, it is generally assumed that the contamination rate for aseptically manufactured preparations might amount to about $10^{-3}$. Since, on one hand, the extent of sterility tests for quality control of lots according to the pharmacopeias is limited and, on the other hand, contaminations may be caused as artifacts while carrying out the test itself, it is difficult to demand sterility in an absolute sense or to test a particular product for it. Therefore, the sterility of the composition should be understood herein such that the composition meets the requirements with respect to sterility of the relevant pharmacopeia.

An active agent is a substance or mixture of substances which can be used for therapeutic, diagnostic, or prophylactic purposes, or for achieving or maintaining general health and well-being. The active agent can be a chemically defined synthetic ("small") molecule, a naturally derived or synthetic peptide, a protein, a polysaccharide, or a nucleic acid such as RNA or DNA. The active agent may also be referred to as active compound, drug, drug substance, medicinal substance, therapeutic agent, and the like.

According to the invention, the active agent is not a surfactant, such as lung surfactant or a surfactant to substitute lung surfactant. Preferably, the active agent is also not a substance which is commonly also used as a pharmaceutical adjuvant and whose effect on the organism is predominantly due to its physical properties.

The active agent is poorly water-soluble. In this context, a poor solubility means that the active compound is poorly soluble in aqueous media at room temperature and relatively neutral pH, for example, at pH 4 to 10, and in particular at pH 4 to 8. Moreover, poorly water-soluble means that at least 30 parts of water or aqueous solvent are required for dissolving one part of active agent. This corresponds to substances which are to be characterized by the commonly used terms "sparingly soluble". "slightly soluble", "very slightly soluble", "practically insoluble" and "insoluble". As used herein, poorly water-soluble and poorly soluble refer to the same property.

Poorly soluble active agents also comprise poorly soluble derivatives or salts of active agents, of which more soluble salts or derivatives may exist. The invention is particularly advantageous for the formulation of active agents which have a saturation solubility in water at room temperature of not more than about 0.1 wt-%. Moreover, active agents of the categories "very slightly soluble", "practically insoluble" and "insoluble" are particularly preferred.

The composition of the invention comprises a non-ionic surfactant component. As used herein, a component of the composition refers to a single substance or to a mixture of substances. Surfactants are amphiphilic, surface- or interface-active materials. Such compounds have at least one relatively hydrophilic and at least one relatively hydrophobic, or lipophilic, molecular region. They accumulate at phase interfaces and reduce surface tension. Surfactants are often used, inter alia, in order to stabilize multi-phase systems. Non-ionic surfactants are surfactants which have no real ionic charge in aqueous media at substantially neutral pH (for example, between pH 4 and 10), but, at most, partial charges. A surfactant may also be referred to as a detergent or tenside, or, to denote its particular function in a composition, as an emulsifier or wetting agent.

Suitable non-ionic surfactants include, in particular, those which are to be considered safe for oral or nasal inhalation or oromucosal administration. Examples of non-ionic surfactants which appear to have a particularly good physiological compatibility are tyloxapol, polysorbates such as polysorbate 80, vitamin E-TPGS, and macrogol hydroxystearates such as macrogol-15-hydroxystearate. If inhalation and pulmonary delivery are intended, it is presently preferred that the composition of the invention comprises at least one of these surfactants.

As mentioned above, the non-ionic surfactant component may also comprise two or even more surfactants, such as polysorbate 80 in combination with vitamin E-TPGS. It has been observed that the effect of non-ionic surfactants on the properties of the composition, in particular the solubilizing effect on poorly soluble active agents, can be additive. This means that by incorporating two non-ionic surfactants instead of only one in the non-ionic surfactant component can achieve a desired effect on the formulation at a lower concentration of each of the surfactants, which may be useful to avoid the occurrence of adverse effects caused by a higher content of only one particular surfactant.

Phospholipids are defined as amphiphile lipids which contain phosphorus. Known also as phosphatides, they play an important role in nature, in particular, as double layer-forming constituents of biological membranes. Phospholipids which are chemically derived from phosphatidic acid occur widely and are also commonly used for pharmaceutical purposes. This acid is a usually (doubly) acylated glycerol-3-phosphate in which the fatty acid residues may be of different length. The derivatives of phosphatidic acid include, for example, the phosphocholines or phosphatidylcholines, in which the phosphate group is additionally esterified with choline, furthermore phosphatidyl ethanolamines, phosphatidyl inositols etc. Lecithins are natural mixtures of various phospholipids which usually have a high proportion of phosphatidyl cholines.

Depending on the source of a particular lecithin and its method of extraction and/or enrichment, these mixture may also comprise significant amounts of sterols, fatty acids, tryglycerides and other substances.

Suitable phopholipids are also those which are suitable for administration by inhalation on account of their physiological properties. These comprise, in particular, phospholipid mixtures which are extracted in the form of lecithin from natural sources such as soja beans or chickens egg yoke, preferably in hydrogenated form and/or freed from lysolecithins, as well as purified, enriched or partially synthetically prepared phopholipids, preferably with saturated fatty acid esters. Particularly preferred are purified, enriched or partially synthetically prepared medium- to long-chain zwitterionic phospholipids which are mainly free from unsaturations in the acyl chains and free from lysolecithins and peroxides. Of the phospholipid mixtures, lecithin is particularly preferred. Examples for enriched or pure compounds are dimyristoyl phosphatidyl choline (DMPC), distearoyl phosphatidyl choline (DSPC) and dipalmitoyl phosphatidyl choline (DPPC). Of these, DMPC is currently more preferred. Alternatively, phospholipids with oleyl residues and phosphatidyl glycerol without choline residue are suitable for some embodiments and applications of the invention.

Depending on which structures are to be formed and which further pharmaceutical effects are to be achieved, the weight ratio between the non-ionic surfactant component and the phospholipid component must be determined or optimized with regard to the selection of the surfactants. According to the invention, a weight ratio of about 5:1 to about 1:20 is presently preferred. With many surfactant-phospholipid combinations, a particularly good solubilization is achieved at a ratio of about 1:1 to about 1:10. For example, if a lecithin is selected as phospholipid component and polysorbate 80 or vitamin E TPGS, or a combination of both, is selected as non-ionic surfactant component, a particularly suitable weight ratio is in this region of about 1:1 to about 1:10. In the case of a combination of two surfactants forming the non-ionic surfactant component, the ratio must obviously be calculated on the basis of the sum of the two surfactants. Especially, poorly soluble corticoids such as budesonide can be solublized surprisingly well in this way.

The composition of the invention may of course comprise further excipients, such as one or more solvents, co-solvents, acids, bases, buffering agents, osmotic agents, stabilizers, antioxidants, taste-masking agents, flavors, sweetening agents, ionic surfactants, thickeners, coloring agents, fillers, and bulking agents.

Solvents and co-solvents, other than water, should be avoided if possible if the composition is intended for inhalation. If the incorporation of a solvent cannot be avoided, the excipient should be selected carefully and in consideration of its physiological acceptability. For example, if the composition is designated for the treatment of a life-threatening disease, the use of some limited amount of ethanol, glycerol, propylene glycol or polyethylene glycol as a non-aqueous solvent may be acceptable. According to the presently more preferred embodiments, however, the composition of the invention is substantially free of these solvents, and in particular of glycerol, propylene glycol or polyethylene glycol, at least if it is used for inhalation purposes. Some organic solvents may be acceptable, on the other hand, if the composition is used as an aerosol which is sprayed onto the oral mucosa, such as to treat aphthae.

In order to provide a well tolerated aerosol, the preparation according to the invention should be adjusted to a euhydric pH value. The term "euhydric" already implies that there may again be a contradiction between pharmaceutical and physiological requirements so that a compromise has to be found which, for example, guarantees that the preparation is, from an economical point of view, just sufficiently stable during storage but, on the other hand, largely well tolerated. Preferably, the pH value lies in the slightly acidic to neutral region, i.e., between pH values of about 4 to 8. It is to be noted that deviations towards a weakly acidic environment can be tolerated better than shifts of the pH value into the alkaline region. A pH value in the range of about 4.5 to about 7.5 is particularly preferred.

For adjusting and, optionally, buffering pH value, physiologically acceptable acids, bases, salts, and combinations of these may be used. Suitable excipients for lowering the pH value or as acidic components of a buffer system are strong mineral acids, in particular, sulfuric acid and hydrochloric acid. Moreover, inorganic and organic acids of medium strength as well as acidic salts may be used, for example, phosphoric acid, citric acid, tartaric acid, succinic acid, fumaric acid, methionine, acidic hydrogen phosphates with sodium or potassium, lactic acid, glucuronic acid etc. However, sulfuric acid and hydrochloric acid are most preferred. Suitable for raising the pH value or as basic component for buffer system are, in particular, mineral bases such as sodium hydroxide or other alkali and alkaline earth hydroxides and oxides such as, in particular, magnesium hydroxide and calcium hydroxide, ammonium hydroxide and basic ammonium salts such as ammonium acetate, as well as basic amino acids such as lysine, carbonates such as sodium or magnesium carbonate, sodium hydrogen carbonate, citrates such as sodium citrate etc.

In one of the preferred embodiments, the composition of the invention contains a buffer system consisting of two components, and one of the particularly preferred buffer systems contains citric acid and sodium citrate. Nevertheless, other buffering systems may also be suitable.

Not primarily for physiological, but for pharmaceutical reasons the chemical stabilization of the composition by further additives may be indicated. This depends mainly on the kind of the active agent contained therein. The most common degradation reactions of chemically defined active agents in aqueous preparations comprise, in particular, hydrolysis reactions, which may be limited, primarily, by optimal pH adjustment, as well as oxidation reactions. Examples for active agents which may be subject to oxidative attack are those agents that have olefinic, aldehyde, primary or secondary hydroxyl, ether, thioether, endiol, keto or amino groups. Therefore, in the case of such oxidation-sensitive active agents, the addition of an antioxidant, optionally in combination with a synergist, may be advisable or necessary.

Antioxidants are natural or synthetic substances which prevent or interrupt the oxidation of the active agents. These are primarily adjuvants which are oxidizable themselves or act as reducing agents, such as, for example, tocopherol acetate, reduced glutathione, catalase, peroxide dismutase. Synergistic substances are, for example, those which do not directly act as reactance in oxidation processes, but which counteract in oxidation by an indirect mechanism such as the complexation of metal ions which act catalytically in the oxidation, which is the case, for example, for EDTA derivatives (EDTA: ethylenediamine tetraacetic acid). Further suitable antioxidants are ascorbic acid, sodium ascorbate and other salts and esters of ascorbinic acid (for example, ascorbylpalmitate), fumaric acid and its salts, malic acid and its salts, butyl hydroxy anisole, propyl gallate, as well as sulfites such as sodium metabisulfite. Apart from EDTA and its salts, citric acid and citrates, malic acid and its salts and maltol (3-hydroxy-2-methyl-4H-pyran-4-one) may also act as chelating agents.

In one of the preferred embodiments, the composition contains at least one antioxidant. In a further embodiment, it contains both an antioxidant and a chelating agent. The combination of a vitamin E derivative, in particular, vitamin E acetate, with an EDTA derivative, in particular, EDTA disodium salt, is particularly preferred. In the case of certain active agents, this combination has proven to be particularly advantageous for obtaining high chemical stability and durability of the composition. In particular, in combination with the active agent budesonide, this combination of excipients is preferred.

In order to well-tolerated, an aerosol should, as far as possible, have a physiologic tonicity or osmolality. Thus, it may be desirable to incorporate into the composition of the invention, an osmotically active excipient to control the osmolality of the aerosol. The content of this excipient (or excipients, if a combination of substances is used) should be selected to yield an osmolality of the aerosol which does not deviate too much from that of physiological fluids, i.e., from about 290 mOsmol/kg. However, in individual cases, a compromise has again to be found between the physical-chemical or pharmaceutical needs on one hand and the physiological requirements on the other hand. In general, an osmolality in the range of about 200 to 550 mOsmol/kg and, in particular, in the range of about 220 or 230 up to about 350 mOsmol/kg may be considered acceptable.

If the active agent and the surfactants contained in the composition give an osmolality below the required or desired value it can be adjusted to the desired value by the addition of one or more suitable osmotically active excipients. Such compounds are, in particular, innocuous mineral salts which react largely neutrally (unless such adjuvants are, at the same time to adjust or buffer the pH value), such as sodium, calcium or magnesium chloride, sulfate or phosphate. One of the particularly preferred members of these is sodium chloride. It was shown, that a minimum chloride concentration of 31 mmol was regarded advantageous [Weber et al.: Effect of nebuliser type and antibiotic concentration on device performance. Pediatric Pulmonology (1997), 23, 249-260]

Further preferred excipients for this purpose are magnesium and calcium sulfate and chloride. It is known that these calcium and magnesium salts can have a positive or auxiliary influence in the inhalation of active agent solutions, possibly because they themselves counteract the local irritations caused by the administration and exert a bronchodilatory effect which is currently postulated in the clinical literature (for example, R. Hughes et al., Lancet, 2003; 361 (9375): 2114-7). Especially magnesium sulfate shows excellent pulmonary tolerance.

As an alternative to the neutral mineral salts, physiologically safe organic compounds may be used as isotonizing agent. Particularly suitable are water soluble substances with a relatively low molecular weight, for example, with a molecular weight of less than 300 or, better still, less than 200 and with a correspondingly high osmotic activity. Examples for such excipients are sugars and sugar alcohols, in particular, trehalose, mannitol, sobitol and isomalt.

Among the less preferred excipients are preservatives, at least if the designated use of the composition is inhalation. Therefore, in one of the embodiments, the composition is substantially free of preservatives. However, if the intended use is topical, nasal or oromucosal administration, a preservative may be considered acceptable. But also if the composition, or a medicament comprising the composition, is for inhalation and is to be packaged in multiple unit dose containers, it may be necessary in order to maintain sterility that a preservative is used.

In one of the preferred embodiments, the composition of the invention is provided in aqueous liquid form. Alternatively, it may be provided in form of a dry solid material which is adapted for preparing an aqueous liquid which can be administered as an aerosol. If the chemical and physical stability of the active agent and the composition permit, it is preferred that the composition is provided in liquid form. If an acceptable shelf life cannot be achieved, the composition must be formulated as a dry solid, such as a powder or lyophilizate for reconstitution.

As used herein, aqueous liquids are liquid compositions in which the liquid carrier or solvent consists predominantly of water and which contain, apart from the carrier at least one further substance which serves a active or auxiliary agent. The liquid state means that the preparation is either a liquid single-phase system or a multi-phase system but having a coherent liquid phase. Thus, the aqueous liquid according to the invention may represent an aqueous solution, a colloidal solution, a suspensions or an emulsion.

Even though the liquid carrier is predominantly water, it can, in individual cases, contain one or more liquids which are at least partially miscible with water, such as ethanol, glycerol, propylene glycol or polyethylene glycol. For example, if the composition is designated to be sprayed—as an aerosol—onto the oral mucosa to treat a condition affecting the mucosa, the incorporation of some non-aqueous solvent or co-solvent may be acceptable. If the designated use is oral or nasal inhalation, however, it is preferred that the composition is substantially free of non-aqueous liquids.

Even though the aerosolization of emulsions and suspensions is possible, the aqueous liquid from represents a solution, or a colloidal solution or dispersion, according to a more preferred embodiment of the invention. In fact, it is the particular advantage of the combination of a non-ionic surfactant component and a phospholipid component which has been found to be highly useful for creating stable colloidal single-phase systems in which a poorly water-soluble compound can be solubilized.

Colloidal solutions, or dispersions, are defined herein as monophasic systems, unlike e.g. suspensions which contain a dispersed solid phase. The rationale behind this is that the colloidal material dispersed within a colloidal solution or dispersion (as used herein, these are interchangable) does not have the measurable physical properties usually associated with a solid material; furthermore, it does not provide a true solid-liquid interphase.

In a colloidal system, not all components are molecularly dispersed; at least one of them is colloidally dispersed. Usually, colloidal structures are understood as being in a size range below about 1 μm, as commonly understood, or between 1 and about 500 nm as defined in other sources (H. Stricker, Physikalische Pharmazie, 3rd Edition, page 440). Therefore, colloidal structures are practically not visible with a light microscope and do not result in market turbidity of the solution, but rather in opalescence. However, the size limits given above are not rigid since they will depend to some extent on the properties under consideration. This nomenclature can be applied to coarser systems, especially when a gradual transition of properties is considered.

According to one of the embodiments of the invention, the composition comprises colloidal structures with an average size of up to about 1 μm (as measured by photon correlation spectroscopy). In a more preferred embodiment, the average diameter is from about 10 nm to about 200 nm. In a further preferred embodiment, it is from about 10 nm to about 100 nm.

The colloidal structures should preferably have a relatively narrow size distribution. For example, if the composition contains liposomes and if it is intended to include a step of sterile filtration in the manufacture of the composition, the average diameter of the liposomes should preferably be below about 200 nm but also rather narrowly distributed in order to allow the sterile filtration procedure without problems such as drug loss or changes in the composition due to the retention of a substantial fraction of larger liposomes. A suitable parameter describing the distribution of the diameter of the colloidal structures is the polydispersity index. It is preferred that the polydispersity index is below about 0.5. More preferably, the polydispersity index is below about 0.3. In a further embodiment, it is below 0.2, such as about 0.1 to about 0.1, or even below 0.1.

A relatively low polydispersity index, reflecting a narrow size distribution, can be achieved by methods generally known to technically qualified persons. For example, liposomal solution may be sonicated, homogenized (optionally with the use of high pressure), or extruded through membranes under moderate pressure. Dialysis or centrifugation can be used as methods to isolate more narrow fractions of colloidal structures.

The respective compositions are not only characterized by the presence of colloidal structures, but also by the low content or even absence of larger particles. In particular, larger particles capable of sedimentation, or particles of solid material should preferably be absent.

Colloidal structures of various types are known to exist in different types of colloidal liquids. In isotropic colloidal solutions, the properties of the solution are the same regardless of the direction of measurement. In other words, in the isotropic state, all directions are indistinguishable from each other. For example, a micellar solution may be isotropic. In anisotropic colloidal solutions, there is orientation and/or alignment of molecules which causes the physical properties of the solution to vary for different directions of measurement. Such anisotropic solutions are referred to as liquid crystals, or liquid-crystalline phases, or mesophases.

Although the inventors do not wish to be bound by a particular theory, it is believed that, depending on the selected type, content and ratio of excipients, in particular of the non-ionic surfactant component and the phospholipid component, various colloidal structures may be generated within the aqueous system of the composition.

In some cases, for example, micelles or mixed micelles may be formed by the surfactants, in which poorly soluble active agents can be solublized. In general, micelles are understood as substantially spherical structures formed by the spontaneous and dynamic association of amphiphilic molecules, such as surfactants. Mixed micelles are micelles composed of different types of amphiphilic molecules. Both micelles and mixed micelles should not be understood as solid particles, as their structure, properties and behavior are much different from solids. The amphiphilic molecules which form the micelles usually associate temporarily. In a micellar solution, there is a dynamic exchange of molecules between the micelle-forming amphiphile and monomolecularly dispersed amphiphiles which are also present in the solution.

The position of the drug molecules which are solublized in such micelles or mixed micelles depends on the structure of these molecules as well as the surfactants used. For example; it is to be assumed that particularly non-polar molecules are localized mainly inside the colloidal structures, whereas polar substances are more likely to be found on the surface.

If the composition of the invention is provides as a micellar or mixed micellar solution, it is preferred that the average size of the micelles is less than about 200 nm (as measured by photon correlation spectroscopy), such as from about 10 nm to about 100 nm. Particularly preferred are micelles with average diameters of about 10 to about 50 nm.

If formulated with a relatively high content of the phospholipid component, and/or if the composition has a relatively low weight ratio between the non-ionic surfactant component and the phospholipid component, such as e.g. about 1:5 or 1:10, the colloidal structures which form may represent liposomes instead of micelles. Liposomes are usually somewhat larger than micelles, but the main difference is that their amphiphilic constituents (which are predominantly amphiphilic lipids such as phospholipids) associate in the form of vesicular, concentric bilayer membranes. Liposomes may comprise only one bilayer, or they may contain several bilayer membranes with different diameters.

Methods for the preparations and characterization of liposomes and liposome preparations are known as such to the skilled person. Often, multilamellar vesicles will form spontaneously when amphiphilic lipids are hydrated, whereas the formation of small unilamellar vesicles usually requires a process involving substantial energy input, such as ultrasonication or high pressure homogenization. Further methods for preparing and characterizing liposomes have been, for example, described by S. Vemuri et al. [Preparation and characterization of liposomes as therapeutic delivery systems: a review. Pharm Acta Helv. 1995, 70(2):95-111].

Of the known liposomes, those are preferred according to the invention which have a predominantly colloidal size, i.e., whose average particle size lies below about 1 µm, and better still at maximally about 500 nm. Highly preferred is a diameter of up to about 200 nm. Such average particle size will usually allow sterile filtration through a filter with a pore size of 0.22 µm, which is a significant advantage in case the composition is not stable enough to withstand heat sterilization.

As mentioned above, it is also preferred that the polydispersity index is relatively low, such as below about 0.5, and more preferably below about 0.3. This is generally true for colloidal structures present in the composition, but also in particular for liposomes, if these are contained in the composition.

The advantageous properties of the composition of the invention, e.g. the superior solubilization capacity for poorly soluble drugs and the taste-masking capability, are closely related to the combination of the non-ionic surfactant component and the phospholipid component. The surfactant content of the composition, both that of the individual surfactants, i.e. the individual non-ionic surfactant(s) and the phospholipid(s), as well as the total surfactants, should be optimized with regard to the intended pharmaceutical effects, but also take into account the physiological tolerability that the composition should have.

The non-surfactants and the phospholipid used according to the invention can fulfill different functions. One of the remarkable effect of the combination, however, is its ability to solubilize poorly soluble active agents in colloidal form and to do so better than this could be achieved by a single surfactant, even at a correspondingly increased concentration within the physiologically acceptable limits (see also Example 1).

The fact that the combination of a non-ionic surfactant with a phospholipid may be pharmaceutically and physiologically acceptable follows, inter alia, from the fact that both tyloxapol and a phospholipid are is contained in the inhalation product Exosurf Neonatal®. The product is used for substitution of pulmonary surfactant in the treatment of acute neonatal Respiratory Distress Syndrome (RDS). Unlike the preparations according to the invention, Exosurf Neonatal® does not contain any further active agent in the usual sense apart from surfactants.

If the composition of the invention is provided in aqueous liquid form, the total content of surfactant in the preparation should be limited to a maximum value of about 5 wt.-% when a pulmonary application is envisaged. If the composition is provided as solid material for reconstitution, the preferences given herein should be recalculated and applied to the respective reconstituted form of the solid composition. For topical, oromucosal or nasal administration, a higher surfactant content may be considered, for example, up to about 10 wt-% or even more than that. For the avoidance of mucosal irritations it would be advantageous to limit the surfactant content to no more than about 5 wt-%.

In the case of pulmonary application, the liquid composition preferably contains a total surfactant concentration of about 0.01 to 5.0 wt-%. Particularly preferred are concentrations of about 0.05 to 2.0 wt-%. However, the optimal amount of surfactants also depends on the active agent, i.e. its physicochemical properties and its concentration in the preparation as well as on the selection of the individual surfactants and the intended effects and product properties. For example, if it is primarily intended to solubilize a poorly soluble active agent such as budesonide and if the one of the preferred non-ionic surfactant components and phospholipid components as mentioned above are selected, the particularly preferred total surfactant content is in the range of about 1 to 5 wt-%, especially at about 1 to 3 wt.-%. If, however, it is primarily intended to improve the organoleptic properties of the preparation, a markedly lower surfactant concentration may be sufficient and, therefore, pharmaceutically more advantageous, for example, a content of not more than about 1.0 wt-%, and, even better, one of not more than about 0.5 wt-%.

Again, if the composition is a solid for reconstitution with an aqueous carrier, these values should be applied to the reconstituted liquid composition and recalculated accordingly. This principle should also be applied to all other quantitative guidances given herein with regard to the composition of the invention in liquid form.

The content of the non-ionic surfactant component in the liquid composition is also preferably in the range of 0.01 to about 5 wt.-%. In a further embodiment, it is in the region of about 0.05 to about 2 wt.-%. This further embodiment is particularly preferred if the composition is meant for oral or nasal inhalation. Another highly preferred content is from about 0.1 to about 1 wt.-%. This range is particularly preferred for compositions in which the active agent is an immunmodulator, such as cyclosporine or tacrolimus and/or a corticosteroid such as, budesonide or ciclesonide and the non-ionic surfactant component comprises at least one of the group consisting of tyloxapol, polysorbates (especially polysorbate 80), vitamin E TPGS, and macrogol-hydroxystearates. If the non-ionic surfactant component comprises more than one surfactant, these FIGURE relate to the content of the total non-ionic surfactants.

The phospholipid component is preferably incorporated in the (liquid) composition of the invention at a content in the range of about 0.5 to about 5 wt.-%. In another embodiment, the content is from about 0.5 to about 3 wt.-%. Again, if the designated use is not inhalation, but e.g. topical or oromucosal administration, the phospholipid content may be higher than this. In the case of compositions for the pulmonary administration of a poorly soluble corticosteroid such as budesonide, a particularly suitable content range is from about 1 to about 3 wt.-%. This is especially true if a lecithin is selected as phospholipid.

The weight ratio between the non-ionic surfactant component and the phospholipid component which presently appears to be highly useful is from about 5:1 to about 1:20. If a poorly soluble corticosteroid such as budesonide is the active agent, if the non-ionic surfactant component comprises at least one of the group consisting of tyloxapol, polysorbates (especially polysorbate 80), vitamin E TPGS, and macrogol-hydroxystearates, and if the phospholipid component comprises at least one lecithin, a particularly preferred ratio is in the range of about 1:1 to about 1:10.

In selecting the surfactants, the surfactant content and the ratio thereof to the active agent content, the effects on the physicochemical properties of the preparation have to be taken into consideration, which are important for the nebulization to give an aerosol which can be administered by inhalation. These comprise, in particular, surface tension and dynamic viscosity.

Especially for pulmonary application, the surface tension of the composition of the invention should be adjusted to the range of about 25 to 80 mN/m, and preferably to the range of about 30 to 75 mN/m. In this connection it is to be taken into consideration that, in the lowest part of this range, a particularly good spreadability of the preparation in the respiratory tract is to be expected, but that the quality of the aerosol and the efficiency of the nebulization may be adversely affected. On the other hand, at the surfactant content required for the colloidal solubilization of a poorly soluble active agent it can hardly be avoided that the surface tension is reduced fairly markedly below that of water or physiological buffer solution. Thus, a compromise has to be found in each case depending on the active agent and the intended application. Especially for the solubiliztion of poorly soluble active agents a surface tension in the range of about 40 to 70 mN/m or, if achievable, even 30 to 50 mN/m is preferred.

The dynamic viscosity also has a clear influence on the particle size distribution of the aerosol formed by nebulization and on the efficiency of nebulization. It should be adjusted to a range of about 0.8 to about 3 mPas. A dynamic viscosity in the range of about 1.0 to about 2.0 mPas is particularly preferred.

As discussed further above, the composition of the invention, if provided in aqueous liquid form, should have a physiologically acceptable, i.e. euhydric, pH value. If provided as a solid for reconstitution, it should be designed to yield such euhydric pH value upon reconstitution. The term "euhydric" already implies that there may again be a contradiction between pharmaceutical and physiological requirements so that a compromise has to be found which, for example, guarantees that the preparation is, from an economical point of view, just sufficiently stable during storage but, on the other hand, largely well tolerated. Preferably, the pH value lies in the slightly acidic to neutral region, i.e., between pH values of about 4 to 8. It is to be noted that deviations towards a weakly acidic environment can be tolerated better than shifts of the pH value into the alkaline region. A pH value in the range of about 4.5 to about 7.5 is particularly preferred. Alternatively, a pH value in the range of about 4 to about 6 is preferred for compositions comprising certain active agents which are more soluble or stable at a rather acidic pH. For example, in the case of compositions comprising budesonide it was found that useful compositions had a pH in the acidic region, such as around pH 4.5.

If the designated use is pulmonary administration, the osmolality of the composition in aqueous liquid form should not deviate too much from that of physiological fluids, i.e., from about 290 mOsmol/kg. However, in individual cases, a compromise may be desirable to reconcile the pharmaceutical needs on one hand and the physiological requirements on the other hand. In general, an osmolality in the range of above about 200 and below about 500 or 550 mOsmol/kg seems useful, and, in particular, in the range of about 220 or 230 up to about 350 mOsmol/kg may be considered acceptable.

As mentioned above, the concentration of the active agent must of course also be taken into account. Very low dosed active agents can generally be solublized and their taste can be masked with lower surfactant concentrations. Furthermore, lower surfactant amounts are sufficient in order to attenuate the irritating effects on mucosa, and the properties causing coughing and bronchiole spasms.

A preferred weight ratio between surfactant content (i.e., total content of surfactant and phospholipid) and active agent content is at least about 1:1, particularly preferred at least about 5:1 for the solubilization of some poorly soluble active agents ratios of more than 10:1 may be necessary. Thus, in a preferred embodiment, for the solubilization of the poorly soluble active agent budesonide a ratio of about 10:1 to 100:1 is to be selected. Markedly lower surfactant/active agent ratios will usually be sufficient when no colloidal solubilization of the active agent is desired or required and the surfactant mixture solves predominantly for masking undesirable organoleptic or physiological properties of the active agent or for improving the spreading of the aerosol in the respiratory tract.

Correspondingly, the composition of the invention, when provided in liquid form or after reconstitution from a solid form, usually comprises a poorly-soluble active agent at a content of about 0.001 to about 1.0 wt.-%, and more preferably at a content of about 0.01 to about 1.0 wt.-%. If the intention of carrying out the invention is not that of solubilizing a poorly soluble active agent but, inter alia, to mask the taste of a poorly tasting compound, the content may be higher.

In a further preferred embodiment, the poorly soluble active agent is selected from the group of corticoids (synonym: corticosteroids), betamimetics, anticholinergics, immunomodulators, anti-infectives (including antibiotics, virustatics and antimycotics), and cytostatics. Highly preferred are active agents from the group of poorly water-soluble corticosteroids. These include, e.g., budesonide, fluticasone, mometasone, beclomethasone, ciclesonide, and flunisolide, or the poorly soluble salts, prodrugs, or derivatives of the respective active moieties. A particularly preferred corticosteroid is budesonide.

In the case of budesonide, a colloidal solution with a content of active agent of about 0.05 to 0.5 mg/ml is particularly preferred and even more preferred is a content of about 0.1 mg/ml to about 0.5 mg/ml. In another embodiment, the content of budesonide is about 0.2 mg/ml to about 0.4 mg/ml, such as about 0.3 mg/ml. As mentioned, budesonide is present in such composition in a colloidally dissolved or dispersed state. In this embodiment, a physiologically well tolerated composition is provided, which, unlike known budesonide preparations for inhalation, can be nebulized quickly, efficiently and without major losses of active agent by means of modern nebulizers including nebulizers operating with a perforated, vibrating membrane, to give fine, high-quality aerosols which are also suitable for pediatric application.

In addition to the aforementioned advantages or the formulation of poorly soluble active agents, the preparations according to the invention provide further advantages and possibilities of application. The inventors have found in tests on probands that preparations with a combination of a non-ionic surfactant and a phospholipid are, surprisingly, capable of masking the bad taste of active agents in inhalation. A distinctly bad taste is extremely unpleasant and irritating in inhalation and it can result in non-compliance, and thus, therapy failure. The bad taste is perceived by the patient through the part of the aerosol which precipitates in the oral and pharyngeal region during inhalation. Even if it can be achieved by optimizing the particle size of the aerosol that as low a fraction of the preparation precipitates there (this fraction is also lost for therapy, unless the oral pharyngeal or nasal mucosa are the tissue to be treated) it is presently hardly possible to reduce this fraction to such an extent that the bad taste of an active agent would no longer be perceived. Therefore, the masking of taste provided by the combination of adjuvants in the preparation is particularly advantageous.

Accordingly, in a further preferred embodiment, the preparation according to the invention contains an active agent which tastes bad. A bad taste can be of different characters which are all comprised herein, for example, sour, hot, metallic, acrid, foul, spoiled, anesthetic etc. Unlike in other embodiments of the invention, the active agent with bad taste can have arbitrary solubility in water. Preferably, the active agent belongs to the group of corticoids, betamimetics, anticholinergics, anesthetics and anti-infectives. An active agent which is particularly preferred in this context is the antibiotic tobramycine including its salts and other derivatives.

Sometimes, but not necessarily, bad taste is accompanied be mucosal irritations caused by the substance. This occurs in various degrees which, in the case of application by inhalation, may range from slight irritation of the pharynx and/or respiratory tract to cough, fits of coughing, bronchoconstrictions and bronchospasms. The inhalation experiments carried out by the inventors with such substances, surprisingly, indicate that these undesirable effects can also be attenuated or masked by the embodiment of the preparation according to the invention. In a further embodiment of the invention, the preparation accordingly contains an active agent which is irritating to the mucosa or causes coughing or bronchoconstrictions. This active agent can have arbitrary water solubility. In this connection, active agents from the group of corticoids, betamimetics, anticholinergics, anesthetics and antiinfectives are again preferred.

A preferred active agent from this category is the antibiotic tobramycine including its salts and derivatives. It is known that this bitter tasting active agent can stimulate salivation and can cause, when adminstered as a very dense aerosol bolus, coughing and bronchoconstrictions, when it is applied in the form of the known preparations [A. Coates et al. Accounting for Radioactivity before and after Nebulization of Tobramycin to insure Accuracy of Quantification of Lung Deposition: Journal of Aerosl medicine (2000), 13, 3, 169-178]

In a further embodiment, the composition contains at least one further active agent. This may be advantageous, for example, in asthma therapy when more than one active agent must be inhaled for therapeutic reasons and the application by the patient in a short time is to be made possible. Important combinations of active agents in this connection are, for example, (a) a betamimetic and a parasympatholytic, (b) a betamimetic and a corticoid, and (c) a parasympatholytic and a corticoid. Further combinations may be offered by mast cell stabilizers such as cromoglicinic acid or nedocromile including their therapeutically useful salts. Combinations of antibiotics and bronchodilators as well as mucolytic may also be useful. The addition of physiologically safe and well tolerated antioxidants such as tocopheroles, catalase, peroxide dismutase is, in principle, useful since these absorb or reduce radical oxygen which is responsible for many inflammatory processes.

According to one of the embodiments comprising more than only one active agent, at least one of these compounds is selected from the group consisting of anti-inflammatory drugs, such as corticosteroids, non steroidal anti-inflammatory drugs (NSAIDs), Leukotriene-Antagonists, Betasympathomimetics, Anticholinergics, Phosphodiesterase-inhibitors, potassium channel openers, Tachikinin and kinin antagonists, IgE-synthesis inhibitors, endothelin-receptor antagonists, anesthetics, immunomodulators, antiinfectives, interferones, Vasodilatators, Angiotension Converting Enzyme (ACE) inhibitors, Cytostatics, in particular: budesonide, ciclesonide, fluticasone, mometasone, beclomethasone, flunisolide; ibuprofen, ketoprofen, valdecoxib, celecoxib; zileuton, montelukast, pranlukast, roflumilast, cilomilast, zafirlukast; albuterol, formoterol, salmeterole, levalbuterole, terbutaline, pirbuterol; tiotropium, oxitropium, ipratropium; theophyllin, pentoxyphyllin, cilomast, rolipram, amrinone, cilostazol, zardaverine, benzafentrine; cromakalim, levocromakalim, pinacidil; Nolpitantium, Saredutant, Nepadutant, Osanetant; Icatibant; Cromoglicate, nedocromil, glucan-sulfates, suplatast, batimastat, omalizumab; idocaine, prolocalne, mepivacaine, bupivacaine, articaine, cyclosporine, tacrolimus, sirolimus, everolimus, rapamycine, leflunomide, midostaurin, azathioprine; chloroquin, hydroxychlorquine; trimethoprim, tetracycline, doxycycline, ciprofloxacine, moxifloxacine, gatifloxacine, carbapenems, azithromycine, clarithromycine, erythromycine, ketolides, penems, aninoglycosides, tobramyicin, filgrastim, pentamidine, microcidin, clerocidin; metronidazole, ketoconazole, itraconazole, voriconazole, clotrimazole, bifonazole, fluconazole, amphotericine B, natamycine, nystatine, amikacine, aciclovir, famciclovir, valaciclovir, didanosine, saquinavir, ritonavir, lamivudine, stavudine, zidovudine, ribivarine, captoprile, lisinoprile, perindoprile, trandolaprile, cilazaprile, lovastatin, relaxin; suramin; sildenfafil, tardalafil, vardenafil, nitrendipin, amlodipine, prostacyclins, beraprost, Iloprost, bosentane, carmustine, lomustine, taxol, etopside, cisplatin; reduced glutathione, TNF-alpha-antibodies including the pharmaceutically acceptable derivatives of these substances such as, for example, the salts, conjugates, enantiomers, racemates, epimers, diastereomers or complexes of any one of these active agents.

Apart from therapeutically active agents, there may also be selected active agents which are primarily intended to serve diagnostic or prophylactic purposes or to promote general well being. Accordingly, the preparation according to the invention can be intended for therapeutic, diagnostic and prophylactic use. The therapeutic use is particularly preferred.

As mentioned above, the composition of the invention may be provided and formulated as an aqueous liquid. Alternatively, it may be provided and formulated in dry solid form, for example, if the chemical stability of an incorporated ingredient is not sufficient to allow an acceptable shelf life. In this case, the composition may be a powder or a lyophilizate. This may require different, or additional excipients, such as a bulking agent or a lyoprotectant. In one of the more preferred embodiments, the composition is a lyophilisate which is obtainable by freeze drying a liquid composition which has the properties as discussed herein-above.

Furthermore, the solid formulation is adapted to be reconstituted to an aqueous liquid form, which may be achieved, for instance, by combining the solid composition with a suitable aqueous carrier, such as sterile water (e.g. water for injection), sterile sodium chloride solution, sterile buffer solution etc.

The composition of the invention may itself be considered a medicament, or it may be part of a medicament. As used herein, a medicament is broadly defined as a medicinal or drug product used for prophylactic, diagnostic, or therapeutic purposes. The scope of the term is broader than that of a composition, as it may include, for example, the combination of more than one composition, or the combination of a composition with a device. Provided that a composition is the actual drug product which is delivered to the patient or health care provider, it may also be itself understood as a medicament. On the other hand, a composition would also describe a bulk material, whereas the medicament better describes the individual drug product as it is distributed by the pharmaceutical manufacturer.

Thus, according to another aspect of the invention, a medicament comprising the composition of the invention is provided which is packaged for use by a patient or health care provider. In a preferred embodiment, the medicament—or composition—is packaged in single dose primary packaging means. Preferably, it can be dispensed from such packaging means with a dispensing variability of better (i.e. less) than about 20%, preferably of less than about 10% of the labeled dose, or volume.

The volume of a single dose of the medicament is generally in the range of about 0.1 to about 10 ml, but more preferably in the range of about 0.2 to about 5 ml. If budesonide is selected as the active agent, and the designated use is inhalation, the volume of a single dose is preferably about 0.3 to about 2 ml. Particularly preferred volumes are about 0.5 and 1.0 ml, respectively.

The primary packaging means can be glass containers (for example, vials) with closure devices of elastomers such as metal security caps, alternatively they may be plastic vials or blister-like primary packaging systems. An individual primary package may contain a single dose or a multiple thereof. In all cases, however, in which heat sterilization of the preparation is possible and does not result in significant deterioration of quality, it is preferable to use a method which, instead of sterile filtration, comprises the final sterilization of the preparation by a heat sterilization method after filling the primary packing means in accordance with the relevant pharmacopeia.

Suitable primary packaging of plastic are, for example, polypropylene or polyethylene vials (PP-/PE-vials) and cycloolefine copolymer blisters (COC-blisters). Sealed plastic containers such as PP or PE vials may advantageously be formed, filled and sealed by the blow-fill-seal method, which is well known to the technically qualified person in the field. The thus produced containers are suitable, in particular, for liquid goods with a volume starting from about 0.2 ml.

In a particularly patient-friendly embodiment, they may be formed in a bottle or V-shaped design with a closure which can be removed by twisting or bending allowing a dropwise dosing and entire emptying meeting with a dispensing uniformity as claimed by Pharmacopoeias. The thus formed opening through which the liquid content can be removed, may be designed such that it fits onto a luer connection or luer lock connection. Thus, the opening may have a round shape and a diameter which largely corresponds to the outer diameter of a male luer connection. In this way, a common syringe with luer connection could be connected tightly to the container, for example, in order to take up the contents of the container and transfer it to a nebulizer or in order to mix the content of the container with the content of the syringe and subsequently to add it to a nebulizer. Alternatively, the opening may have a smaller diameter, such as the inner diameter of a male luer connective piece, if the opening is within a protrusion which is connectable with a female luer piece.

As a further alternative, it may be envisaged that the plastic container is designed so that, after removing the closure element, it may be connected essentially tightly with a connection piece intended for the addition of liquid of a correspondingly adapted nebulizer, whereby it is possible to fill the preparation directly into the reservoir of the inhaler.

Depending on the intended product application, the medicament may also be presented in multiple unit dose primary packaging means or containers. Such containers may hold a fill volume of about 2 to about 50 ml or even more. If the use is different from inhalation, such product design may be appropriate and cost effective. If the use is oral or nasal inhalation, the medicament must comprise a preservative to ensure its sterility after the withdrawal of a dose. However, the incorporation of a preservative is less preferred for pulmonary administration due to tolerability reasons.

Plastic containers of the above-mentioned kind are advantageous because they can easily be provided with imprints. Thereby, one can firstly do away with paper labels, which is desirable in order to avoid the migration of components of the adhesive, the paper or the printing ink through the container wall into the preparation. Furthermore, important information may be made available to visually impaired patients by such an imprint. The imprint can contain various information, for example, a lot number, a best before date, a product designation, instructions for use or one or more volume or dose markings. Especially for pediatric patients, where a flexible dosing depending on the age and body size is desirable, a plurality of volume markings can serve to facilitate the removal of the desired dose without further implements, thereby reducing the risk of dosing errors.

One or more primary packaging means may be packaged in one secondary packaging means, such as a cardboard box.

As mentioned, in order to increase the storage stability, it may be advantageous to subject the composition according to the invention described above to freeze drying in order to storage in the solid state. The liquid form required for nebulization can be prepared there from shortly before use by mixing with sterile water. Therefore, a solid preparation is also provided in accordance with the invention, which is obtainable by freeze drying the preparation according to the invention described above. The methods of freeze drying are known, as such, to the skilled person.

If the medicament comprises such solid-state composition, it may be useful to provide a secondary package which is in the form of a kit, and which contains one or more primary packaging containers with the solid composition and also one or more containers filled with a suitable aqueous liquid carrier which is to be used for reconstituting the solid composition and form an aqueous liquid system which can be aerosolized, or which is suitable for nasal or oral inhalation.

The manufacture of the composition takes place by a combination of process steps which are known as such and which have to be selected and, if necessary, adapted in view of the special requirements of the active agent and the desired product properties. Apart from general pharmaceutical requirements which apply for all pharmaceutical compositions, the special requirements for compositions for inhalation have to be taken into account. The compositions must be sterile, i.e., free of germs capable of reproduction, which must be ensured by careful selection and carrying out of the process steps. Further requirements may result from special provisions of use. If, for example, the composition is intended for inhalation with a nebulizer of the type operating with a perforated vibrating membrane, it must be ensured by the method of manufacture etc. that the size of the active agent particles (if present) does, in fact, lie below the limit from which an unwanted sieving effect occurs.

If the composition is an aqueous solution, which, as mentioned above, also comprises colloidal, i.e., for example, micellar or mixed micellar solutions, and if no heat sterilization in the final container is possible due to the physical or chemical thermolability of the composition or individual components thereof, sterile filtration may be used as a method of sterilization. Even if the composition is an aqueous suspension such as a microsuspension, the final sterilization may be critical since it may considerably alter the particle size distribution of the suspension particles and, thereby influence important properties of the composition.

In the case of solutions and colloidal solutions, a preferred manufacturing method may comprise the following steps:
(a) providing the ingredients (from which the composition is to be composed of;
(b) preparing an aqueous liquid composition from the ingredients provided in step (a);
(c) sterile filtration of the composition obtained in step (b); and
(d) filling the sterile filtered composition from step (c) into sterile containers under aseptic conditions.

In a variant of the method of the manufacture the ingredients in step (a) are provided in a sterile condition in order to limit the initial germ load of the composition. If not all starting materials can be provided in a sterile condition, at least those should be pre-sterilized for which this is possible without compromising quality.

The manufacture of the aqueous composition from the intended ingredients or starting materials in step (b) can take place in several individual steps. For example, the preparation of an aqueous solution (optionally colloidal solution) of the non-ionic surfactant and the phospholipid as well as, optionally, further adjuvants may take place first. For the formation of a homogeneous colloidal solution it may be advantageous to apply a step with relatively high energy input, for example, a homogenization step under increased pressure (high pressure homogenization), ultrasonication or heating to about 45° C., to about 50-70° C. or even to higher temperatures. In order to reduce the germ load and to increase the efficiency of the subsequent germ reduction measures, one should work with sterilized or germ-reduced starting material and, if possible, under aseptic conditions. Furthermore, it might be indicated to subject the colloidal adjuvant solution prepared in the first part of step (b) to a heat sterilization process.

In a further part of step (b), the active agent would have to be dissolved in the thus prepared colloidal solution, again, if possible, under aseptic conditions. Preferably, this is done without any use of mechanical particle size reduction methods in which solid active agent particles are divided mechanically. On the contrary, it is preferred that an energy input takes place at this stage of the process, if necessary, by heating or, optionally, by ultrasonication. In many cases, however, the incorporation of the active agent may be achieved simply by stirring, even the colloidal dispersion of poorly soluble active agents into micelles or mixed micelles.

In a directly or indirectly subsequent process step, the previously prepared active agent containing solution or colloidal solution is sterile filtered, i.e., filtered through a filter, for example, a membrane filter, with a pore size of about 0.22 μm, optionally with application of pressure, in order to remove the germs and particles contained in the solution. Variants of suitable sterilization methods including the devices used therefore are, in principle, known to the skilled person. It is a particular advantage of the compositions of the invention that they can usually be sterile filtered without any change in composition or loss of active agents, since the active agent is colloidally dissolved or dispersed, instead of being processed as a solid material.

In a further directly or indirectly subsequent process step, the previously sterile filtered solution or colloidal solution is filled, under aseptic condition, into the primary packaging, i.e., the final containers, which are then tightly sealed. As mentioned above, it is a preferred embodiment to manufacture and provide these containers within a blow-fill-seal process. Suitable variants for this process steps and devices therefore are known as such.

The medicaments thus prepared may be used for the diagnosis, prophylaxis or therapy of a symptom, disease, or condition in a mammal. While the veterinary use may be easily possible if the medicament is to be administered as e.g. a topical or oromucosal spray, the more preferred administration is oral or nasal inhalation, and the more preferred subjects are human patients. Particularly preferred is the use involving the administration of the medicament to a pediatric patient, such as a baby, an infant, a child, or a youth or adolescent.

In one embodiment of the invention, the medicament is intended for the topical treatment of the skin or a mucosa. In this case, the medicament will usually be administered as a topical spray. Highly preferred, however, is the use of the medicament of the invention in the management of diseases, symptoms, and conditions affecting the upper and lower airways.

In another embodiment of the invention, the medicament is intended for the treatment of the oral or nasal mucosa, for example, in the case of allergic rhinitis, stomatitis, vasomotoric rhinitis, chronic rhinitis, seasonal rhinitis, perennial rhinitis, nasal polyps, aphthae, or other inflammatory diseases of the oral mucosa. In this case of application, very simple devices for the generation of the aerosol can, in principle, also be used, for example, mechanical atomizers such as those commonly used for oral or nasal sprays. Alternatively, jet, ultrasonic or piezoelectric vibrating membrane nebulizers can also be used for this purpose which may have to be adapted in the case of nasal application.

In a further embodiment, the composition is intended for the treatment of the mucosa of the maxillary, paranasal or frontal sinuses. These mucosas are, in principle, accessible to aerosol therapy. However, the efficient application of an aerosol is difficult and can hardly be carried out with conventional nebulizers due to the poor ventilation of these sinuses. The simple nasal inhalation of an aerosolized active agent composition does take this to the vicinity of the sinuses; however, the entirely predominant part of the aerosol flow passes the ostia to the sinuses without a significant part of the aerosol entering into the sinuses. On the other hand, the frontal and paranasal sinuses are frequently the very sight of inflammatory processes which can be treated with budesonide.

Specially adapted jet nebulizers with which the sinuses may be reached much better than previously have recently become available. These nebulizers have a nose piece for directing the aerosol flow into the nose. If only one nostril is used for inhalation of the aerosol the other nostril must be closed by a suitable device. Furthermore, these nebulizers are characterized in that they release an aerosol with pulsating pressure. The pulsating pressure waves achieve a more intensive ventilation of the sinuses so that a concomitantly inhaled aerosol can spread better into these cavities. Examples for such nebulization devices are disclosed in DE 102 39 321 B3.

In a preferred embodiment, the composition according to the invention is used for the manufacture of a medicament for application by means of one of the devices described therein for the treatment of infections of the upper respiratory tract, in particular, with a device of the PARI Sinus type.

Another preferred use of the medicament of the invention is for a management of a disease, symptom or condition affecting the bronchial system or the lung. Such diseases include inflammatory processes of the lungs and connecting tissue, such as, asthma, pediatric asthma, obstructive bronchitis, chronic obstructive bronchitis, chronic obstructive pulmonary disease (COPD), emphysema, lung infections, vascular, parenchymal lung disease, such as sarcosidosis, pulmonary fibrosis, or cystic fibrosis, or bronchiolitis obliterans caused e.g. after lung transplantation, or pulmonary hypertension and lung cancer. A particularly preferred condition whose treatment can be substantially improved with the invention is pediatric asthma. The invention allows the highly efficient administration of aerosols comprising poorly soluble glucocorticoids such as budesonide to pediatric patients.

As mentioned above, aqueous compositions such as the liquid compositions according to the invention are to be used for the administration as aerosol which is generated in situ, i.e., directly upon use, by a suitable device. Common types of nebulizers with which such compositions can be aerosolized have already been described at the beginning. Jet nebulizers have been used in therapy for a long time and ultrasonic nebulizers have also been used for some time.

Recently, very efficient nebulizers have been developed which are named according to their principle of function, which may be piezoelectric, electro-hydrodynamic and/or based on the vibrating membrane with pores (for example, eFlow™, eFlow Baby™, AeroNeb™, Aero Dose™ or AERx™). The different mechanisms of aerosol generation result in differences in the quality of nebulization for particular compositions.

The compositions according to the present invention are adapted, in particular, to the requirements of nebulization by nebulizers functioning with vibrating membranes (and in particular perforated vibrating membrane nebulizers). A particularly preferred nebulizer for the use of which the composition is intended is the eFlow™ nebulizer of Pari GmbH. This nebulizer and devices of a similar type are particularly suitable for a modern aerosol therapy: they are small and nebulizer relatively large liquid volumes within a short time period and usually give aerosols of particularly high quality. Of course, these nebulizers, too, have limitations or problems in use, for example, when suspensions of poorly soluble active agents are to be nebulized. Because the aerosol generation involves an extrusion of the inhalation liquid through the pores of a vibrating membrane larger solid particles are either completely excluded from aerosolization (when their diameter is at least about as big as the diameter of the pores) or—at particle sizes in the lower micrometer range—they result in at least a more or less marked sieving effect. This results in a lowered active agent concentration in the aerosol which is actually released from the nebulizer and available for inhalation. The present invention is particularly advantageous for the administration of poorly soluble active agents with such nebulizers: thus, these active agents can be formulated and inhaled as colloidal solution instead of micro-suspensions, which essentially obviates or at least markedly reduces the sieving effect by the pores of the membrane.

It has been found that the compositions and medicaments of the invention can be aerosolized in single dose volumes of about 0.2 to about 5 ml very efficiently and effectively by vibrating membrane nebulizers, in particular by the eFlow™ and eFlow™ Baby devices. For example, budesonide-containing medicaments can be nebulized and delivered from these inhalers at a total output rate of more than 0.2 ml or mg per minute, such as in the range of 0.2 to about 0.8 ml, potentially up to about 1.5 g or ml per minute. For example, the total output rate could be in the region of about 0.3 to about 0.6 ml per minute, which is a very useful range. In another embodiment, the total output rate is in the region of about 0.4 to about 0.55 ml per minute. These output rates translate into very short inhalation times, such as less than about 5 minutes for most compositions, and less than about 3, or even 2 minutes for some of the particularly preferred compositions, administered in a volume range of 0:3-1.5 ml. The loss of drug in the devices is low, such as below 15% of the dose filled into the nebulizer, in most cases even less than 10%, and sometimes less than 5%.

Furthermore, it has been found for the compositions of the invention that the delivered dose is substantially proportional to the volume-defined dose which is filled into the eFlow™ device. The dose proportionality of delivery and total output rates allow convenient and flexible dosing based on one composition, which can be dosed by volume. Contrary to jet nebulizers, there is no concentration effect upon inhalation and no saliva can enter the medication cup.

Due to the highly efficient aerosolization performance of the eFlow™ device, the large fraction of respirable aerosol droplets, and the specific properties of the compositions of the invention, another benefit can be achieved: the nominal drug dose can be substantially reduced in comparison to conventional nebulization therapy, typically by about a factor in the range of 2 to 10, and in particular in the range of 3 to 5.

In a further aspect, the invention provides a method for treating a human subject suffering from any lung disease caused by an allergic, inflammatory or gene defect or lung transplantation, such as asthma, pediatric asthma, obstructive bronchitis, and chronic obstructive bronchitis, bronchiolitis obliterans, pulmonary or cystic fibrosis. The method comprises the repeated administration of a sterile aqueous composition comprising a poorly water-soluble immunmodulator and/or corticosteroid, a non-ionic surfactant component and a phospholipid component. According to the method of the invention, the administration is achieved by nebulizing said composition by means of a nebulizer having a vibrating membrane with pores of defined size, and wherein the medicament is delivered from said nebulizer in aerosol form at a total output rate of about 0.2 to about 0.8 ml per minute.

As used herein, the total output rate is defined as the volume or mass of the aerosol which is delivered from the nebulizer in aerosol form.

In one of the preferred embodiments, the method is conducted with a nebulizer which is selected, or adapted, to deliver an aerosol having a mass median diameter of about 1 to about 5 µm, and more particularly of about 2 to about 4 µm. This can be achieved, for example, by using an eFlow® nebulizer.

In another preferred embodiment, the method is conducted with a nebulizer which is selected, or adapted, to deliver an aerosol which is characterized in that at least about 60% of the aerosol consists of particles or droplets having a diameter of from about 2 to about 5 µm. Again, this can be achieved, for example, by using an eFlow®, or an eFlow® baby, nebulizer.

In a further preferred embodiment of the method, budesonide is selected as active agent. The preferences for selecting the non-ionic surfactant component and the phospholipid component comply with those discussed further above in the context of the compositions. In another embodiment, ciclesonide or fluticasone or mometasone is selected. Optionally, a second active compound is present in the composition. Examples of combinations of useful active agents present in the composition of the invention include: (a) a corticosteroid and an immunomodulator; (b) a corticosteroid and a beta-agonist; (c) a corticosteroid and an anticholinergic agent; (d) an immunomodulator and a beta-agonist; (e) an immunomodulator and an anticholinergic agent; (f) a beta-agonist and an anticholinergic agent; as long as one of the active agents is a poorly soluble compound. More specifically, examples combinations of useful active agents include: (g) budesonide and formoterol; (h) budesonide and tiotropium; (i) fluticasone and formoterol; (j) fluticasone and tiotropium; (k) ciclesonide and and formoterol; (l) ciclesonide and tiotropium; (m) mometasone and formoterol; (n) mometasone and tiotropium. Those combinations may have an additive and/or synergistic effect and are particularly useful to improve patient compliance and the efficiency of the drug therapy in distinct patient groups.

The method can involve once-daily or twice-daily administration. If Budesonide, ciclesonide and/or cyclosporine is selected as active agent, once-daily administration is presently preferred, but twice-daily administration is just as feasible. A particularly preferred human subject is a pediatric patient.

According to a particularly preferred embodiment of the method, a human subject suffering from asthma or pediatric asthma is treated by once-daily or twice-daily administration of a sterile aqueous composition comprising: (a) budesonide, (b) a non-ionic surfactant component selected from the group consisting of tyloxapol, polysorbates, vitamin E TPGS, and macrogol hydroxystearates, and (c) lecithin; the administration is achieved by nebulizing said composition by means of a nebulizer having a vibrating membrane with pores of defined size; a single dose of the medicament has a volume of about 0.2 ml to about 1 ml and a budesonide content of about 0.2 to about 0.5 mg/ml; and the composition is delivered from said nebulizer in aerosol form at a total output rate of about 0.2 to about 0.8 ml per minute. In an alternative embodiment, lecithin is replaced by another phospholipid. In a further embodiment, the total output rate is between about 300 and about 600 mg per minute. A preference for both variants is that the human subject is a pediatric patient and that a total daily dose of budesonide ranging from about 50 μg to about 400 μg is administered.

In another embodiment, a human subject suffering from a parenchymal lung disease, such as ideopatic pulmonary fibrosis (IPF), idiopatic interstitiell pneumonia, Sarcosidosis or Bronchiolitis obliterans is treated using a composition of the invention, wherein at least about 200 μg of budesonide are administered, preferably as an aerosol having droplets with a mass median diameter of about 2.0-3.5 μm.

In summary, the combination according to the invention of a non-ionic surfactant and a phospholipid has a distinctly high capacity to solubilize poorly soluble active agents in colloidal form. It is to be assumed that this is associated with the formation of micelles or mixed micelles with a lipophilic nuclear and a hydrophilic outer region. A particular advantage of colloidal solutions such as these is the fact that, as compositions for inhalation, they can be aerosolized better (i.e., without high losses of active agent in the nebulizer) and that aerosols with finer droplet size can be generated than, for example, in the case of microsuspensions. Another advantage is that, by using the specified type of nebulizer to conduct the method, the nebulization efficiency is substantially independent of the breathing pattern of the patient, which is particularly relevant for children of various ages who may have very divers capabilities of conducting breathing maneuvers for inhalation therapy.

An aerosol with low average particle size or with a high fraction of droplets in the lower micrometer range is particularly important if the inhalation is to reach the deeper regions of the respiratory tract, i.e., the fine branches of the bronchioles or even the alveoles. It is also particularly important and advantageous if the patient are children in whom the corresponding anatomical structures are markedly smaller than in adults. In one of the preferred embodiments, the composition is, therefore, intended for application in children, which means babies, infants, children and youth. In particular, the application in young children, babies and infants is preferred.

A further advantage of the micellar and mixed micellar solutions lies in the fact that they can be filtered through a membrane filter with a pore size 0.22 μm in order to remove any germs that may be present (sterile filtration). This method of sterilization is always particularly important when sterilization by heat or radiation appears impossible or disadvantageous for chemical or physical-chemical reasons.

Thus, the advantage of colloidal solutions that may be achieved by the surfactant combination according to the invention compared to micro suspensions such as Pulmicort® suspension for inhalation is obvious. Accordingly, in a particularly preferred embodiment, the active agent is an active agent which is poorly soluble in water.

In respective of whether a therapeutic, diagnostic or prophylactic effect is intended, the active agent can be administered in form of the composition according to the invention to exert its effect locally (for example, in the nose, in the pharynx or the bronchi) on or in the vicinity of mucosa of the respiratory tract or it may have a systemic effect after absorption into the blood circulation. However, in the therapy of diseases of the upper and lower respiratory tract, a rather local effect will be particularly relevant.

It is particularly advantageous to use the composition according to the invention for the manufacture of medicaments which are used for the prophylaxis or treatment of bronchial or pulmonary diseases or symptoms, for example, of bronchial asthma or of chronic obstructive bronchitis. In this case, the composition is preferably intended for inhalation with a jet, ultrasonic or piezoelectric vibrating membrane nebulizer, for example, with a PARI eFlow™ or, in the case of pediatric use, an eFlow Baby™ nebulizer.

EXAMPLES

The following examples serve to illustrate the invention; however, they are not to be understood as the only embodiments of the invention.

Example 1

Solubilization of Budesonide with Tyloxapol and DMPC

Buffered aqueous solutions of tyloxapol, DMPC and tyloxapol in a mixture with DMPC were prepared. The saturation solubility of budesonide in these solutions was measured by adding an excess of budesonide and treating the sample with heat and ultrasound and subsequently allowing it to stand for equilibration. The equilibrated samples were filtered through a membrane filter with a poor width of 0.22 μm and the content of budesonide in the filtrate was determined. Selected results from these experiments are shown in Table 1. The saturation concentration of budesonide in DMPC solutions could not be increased, even by further increasing the DMPC content.

TABLE 1

| Tyloxapol [wt %] | DMPC [wt %] | Budesonide [µg/ml] |
|---|---|---|
| 0 | 1 | 20 |
| 1.5 | 0 | 204 |
| 1 | 0.5 | 268 |

Example 2

Preparation of a Sterile Colloidal Solution of Budesonide

Budesonide is an example for a poorly water soluble active agent which can advantageously be formulated as a colloidal aqueous solution by the combination of surfactants according to the invention.

The starting materials shown in Table 2 were provided in the stated amounts. The stated starting materials, except for budesonide, were fast dissolved or dispersed in the water for injection by stirring with a magnetic stirrer. Subsequently, the batch was homogenized for 10 minutes at 1500 bar with a high pressure homogenizer. This gave an opalescent colloidal solution with a pH of about 4.5.

To this solution, previously provided 200 mg of budesonide were added. This batch was warmed to about 60-70° C. and, at the same time, subjected to ultrasonication for about 30 min. Thereafter, the batch was cooled to room temperature while stirring with a magnetic stirrer. Evaporated water was replaced by a corresponding amount of water for injections. Thus, an opalescent colloidal solution was obtained. Under a laminar flow box with sterile equipment, this was subsequently manually sterile filtered through a membrane filter with a poor size of 0.22 µm and filled into sterile glass vials. The vials were sealed germproof, stored under various temperature conditions and, after various time intervals, tested for decomposition products and physical parameters.

TABLE 2

| Starting material | Amount |
|---|---|
| Budesonide | 0.2 g |
| Tyloxapol | 10.0 g |
| DMPC | 5.0 g |
| Sodium chloride | 8.4 g |
| Citric acid | |
| Sodium citrate | pH = 4.4 ± 0.25 |
| Water for injection | ad 1000 ml |

The characterization of the preparation filled into the vials showed a budesonide content of 202.34 µg/ml, a surface tension of 38.8 mN/m, a dynamic viscosity of 1.07 mPas, an osmolality of 0.282 Osmol/kg and a pH of 4.25 at 21.8° C. The average size of the colloidal particles measured by photon correlation spectroscopy at an angle of 90° C. was 13.1 nm (expressed as z-average) and is indicative of micellar structures.

The advantages of such a colloidal solution of the active agent of budesonide became particularly apparent if it is compared with the commercially available product Pulmicort® Suspension, which shows an average particle size of about 3-4 µm. In contrast to the suspension, the colloidal solution shows behavior typical of solutions and can be nebulized much better. The benefits and advantages of the colloidal budesonide solution according to the invention become particularly apparent in the therapy of asthma and chronic obstructive bronchitis in children and babies.

FIG. 1 shows a markedly improved pulmonary deposition for the colloidal budesonide solution (here referred to as "BUDeFlow™") in vitro using a respiratory tract model of a 9 months old baby (Sophia Anatomical Infant Nose Throat=SAINT Model) and lower unwanted nasal or oropharyngeal deposition than the Pulmicort® Suspension ("Pulmicort"), as is obvious from the relative ratio of the pulmonary dose to the "Cast Deposition". In these investigations, two different nebulizers were used, namely the jet nebulizer PARI LC PLUS® and the piezo-electric nebulizer PARI eFlow® baby. The active agent doses used for the nebulization are stated in the legend. Relative deposition data are shown in Table 3. In vivo investigations with radio actively marked budesonide confirm the better deposition of the colloidal budesonide solution according to the invention as compared the suspension.

TABLE 3

| | PARI LC PLUS ®/PARI BOY ®N | | | |
|---|---|---|---|---|
| | Pulmonary dose | Oroph. deposition | Exhaled fraction | Residue |
| Pulmicort ® (500 µg/2 ml) | 2.0% | 6.8% | 26.1% | 65.2% |
| (100 µg/0.5 ml) | 5.6% | 9.0% | 31.2% | 54.2% |
| | eFlow ™ Baby | | | |
| | Pulmonary dose | Oroph. deposition | Exhaled fraction | Residue |
| Pulmicort ® (500 µg/2 ml) | 12.0% | 13.3% | 31.2% | 43.5% |
| BUDeFlow ™ (100 µg/0.5 ml) | 28.9% | 20.2% | 35.4% | 15.6% |

The colloidal solution obtained can also be employed in the form of a conservative preservative-free nasal spray or with other application devices such as, for example, a jet nebulizer operating with a pulsating compressor, such as, for example, the PARI SINUS™, and can also be used therapeutically for the nasal treatment of paranasal and/or frontal sinusitis or allergic rhinitis.

Example 3

Preparation of a Budesonide Formulation for Nasal Application 3.75 g of tyloxapol were weight into a 1000 ml glass beaker. 486.0 g of water for injection were added and it was stirred at room temperature (20° C.) until the tyloxapol had completely dissolved. 4.23 g of sodium chloride, 0.2 g of citric acid and 0.25 g of sodium citrate were added to the resulting solution. After dissolution of all components, the pH of the solution was adjusted to 4.3 by additional sodium citrate. 7.5 g of lipoid PC 14:14 (dimyristoyl phosphatidylcholine) were added to the solution and homogenized by Ultra Turrax at 11000 rpm (5 minutes). The formulation was subsequently homogenized for 20 minutes by high-pressure homogenization (micro fluidics M100EH) at 1500 bar. The resulting solution showed slight opalescence which nearly disappeared after 12 hours on the magnetic stirrer.

After addition of 400 µg/ml of budesonide, the formulation was again homogenized (Ultra Turrax followed by high pressure homogenization). After further 12 hours standing on the magnetic stirrer, the now slightly opalescent preparation could be sterile filtered through a 0.22 µm membrane filter under aseptic conditions and filled into pump atomizer bottles (100 µl/stroke).

The final budesonide containing formulation at the following physicochemical properties: a pH of 4.3 at 22.7° C., a dynamic viscosity of 1.16 mPas, a surface tension of 40.6 mN/m and an osmolality of 0.262 Osmol/kg.

Example 4

Preparation of a Sterile Solution of Tobramycin

Tobramycin is an example for an active agent with bad taste, which can cause coughing and bronchoconstrictions.

An opalescent colloidal solution of 0.45 g of DMPC, 0.91 g tyloxapol, 0.225 g of sodium chloride in 89.59 g of water for injection was prepared from correspondingly provided amounts. This was done in analogy to Example 2, i.e., the batch was first homogenized under high pressure at 1500 bar without the active agent. To this solution, 5.41 g of 96% sulfuric acid and 10.88 g of tobramycin were added. This initially resulted in precipitation. The batch was subsequently stirred at room temperature for 24 hours with a magnetic stirrer, whereupon a clear, possibly colloidal solution formed, which was sterile filtered and dispensed as described in Example 2. The characterization of the dispensed preparation gave a pH of 6.23 at 21.8° C., a dynamic viscosity of 2.07 mPas, a surface tension of 36.5 mN/m and an osmolality of 0.299 Os-mol/kg.

Example 5

Preparation of a Sterile Solution of Lidocaine 0.55% (w/v) of lidocaine base were incorporated into a solution of the components shown in Table 2 (without budesonide). After a sterile filtration, the colloidal solution was filled into pre-sterilized single dose containers (0.5-3 ml) of glass and polypropylene. Inhalation experiments show that the local anesthetic effect of lidocaine, which is undesirable in this context, was reduced.

Example 6

Preparation of a Sterile Solution of Cyclosporine

This example describes the possibility to solubilize the water insoluble immunomodulator cyclosporine according to the invention.

The starting materials shown in Table 4 were provided in the stated amounts. Cyclosporine is first suspended or dissolved in propylene glycol. This mixture is mixed with aqueous buffer solution which contains the amounts of tyloxapol, DMPC and NaCl, stated in Table 4, and made up to 100 ml with water for injection. By high pressure homogenization, as described above, a colloidal solution is formed, which, after sterile filtration through a 0.22 μm filter, is filled into pre-sterilized 0.5-3 ml single dose containers of glass or polypropylene. The cyclosporine content of the formulation obtained is 570 μg/ml.

TABLE 4

| Starting material | Amount [g] |
|---|---|
| Cyclosporine | 0.06 |
| Tyloxapol | 1.0 |
| DMPC | 1.0 |
| Propylene glycol | 1.0 |
| Sodium chloride | 0.7 |
| Water for injection | ad 100 ml |

The average particle size (z-average) of this colloidal dispersion, determined by photo correlation spectroscopy, is 9.7 nm.

Example 7

Preparation of Combination Products

Combinations of steroids, such as, for example, budesonide, with water insoluble or water-soluble substances from the group of betamimetics (such as, for example, salbutamol, formoterol) and/or anticholinergics (such as, for example, ipratropium, thiotropium) are therapeutically preferred due to a synergistic effect and improve patient compliance. In one batch, formoterol (20μ/ml) and in another batch, ipratropium bromide (100 μg/ml) was incorporated into a budesonide solution (200 μg/ml) prepared according to Example 2. The resulting colloidal solutions were sterile filtered and filled into pre-sterilized 0.5 to 5 ml single dose containers of glass or polypropylene.

Example 8

Preparation of Freeze Dried Combination Product with Vitamin E Acetate and Reduced Glutathione Anti oxidants such as, for example, reduces glutathione and tocopherols (vitamin E derivatives) can reduce inflammatory processes which are induced by radical oxygen. The following example illustrates the possibility to solubilize the water insoluble tocopherol acetate with glutathione, which is water soluble, but, unstable if stored in the dissolved state, by means of the surfactant combination according to the invention and to stabilize by a subsequent freeze drying process.

2 g of tyloxapol, 2 g of DMPC, and 20 mg of tocopherol acetate are mixed with 200 ml of water for injection and pre-homogenized with an Ultra Turrax. The dispersion is homogenized for about 15 minutes in a high-pressure homogenizer at 1500 bar. 2.5 g of reduced glutathione are rapidly dissolved in 50 ml of the resulting colloidal solution with stirring and the pH is adjusted to 6 by addition of lysine monohydrate. The resulting colloidal glutathione-vitamin E acetate solution is immediately sterile filtered into glass vials and subsequently freeze dried. The osmolality of the resulting solution was 0.342 Osmol/kg.

After addition of water for injection, the lyophilisate dissolves completely upon shaking for 10 seconds.

Example 9

Colloidal Solubilization of Budesonide Using Polysorbate and Lecithin

In analogy to example 2, colloidal solutions of budesonide were prepared using polysorbate 80 as non-ionic surfactant component (instead of tyloxapol) and lecithin of the commercial grade, Lipoid S 100, as phospholipid component. Citric acid and sodium citrate were used as buffer system to adjust the pH to 4.5. Sodium chloride (0.846% w/w) was used as osmotic excipient. Disodium edetate (0.01% w/w) was incorporated as stabilizer preventing oxidation.

With polysorbate 80 at a concentration ranging from 0.10 to 0.50 wt.-% and lecithin concentrations ranging from 1.0 to 3.0 wt.-%, it was found that substantial amounts of budesonide could be colloidally solubilized (see table 5). The taste of the samples was acceptable. The average diameter of the colloidal structures ranged from about 40 to about 50 nm, with polydispersity indices of 0.2 to 0.3. The colloidal solution with the lowest concentration of the non-ionic surfactant and phospholipid component (line 1) was also investigated by small angle X-ray scattering, which indicated the presence of colloidal structures which were probably in the form of unilamellar liposomes.

TABLE 5

| Polysorbate 80 [wt. %] | Lipoid S100 [wt. %] | Ratio | Budesonide solubilized [mg/ml] |
|---|---|---|---|
| 0.10 | 1.0 | 1:10 | 0.36 |
| 0.15 | 1.5 | 1:10 | 0.43 |
| 0.25 | 1.5 | 1:6 | 0.47 |
| 0.40 | 1.5 | 1:3.75 | 0.50 |
| 0.50 | 2.0 | 1:4 | 0.83 |
| 0.50 | 3.0 | 1:6 | 1.09 |

Example 10

Colloidal Solubilization of Budesonide Using Vitamin E TPGS and Lecithin

In analogy to example 9, colloidal solutions of budesonide were prepared using vitamin E TPGS as non-ionic surfactant component and lecithin of the commercial grade, Lipoid S 100, as phospholipid component. The other excipients and their content remained the same as in example 9.

With vitamin E TPGS at a concentration ranging from 0.10 to 0.50 wt.-% and lecithin concentrations ranging from 1.0 to 3.0 wt.-%, it was found that substantial amounts of budesonide could be colloidally solubilized (see table 6). The taste of the samples was acceptable. The particles size of the colloidal structures was about 50 to 55 nm, with polydispersity indices of 0.2 to 0.3.

TABLE 6

| Vitamin E TPGS [wt. %] | Lipoid S100 [wt. %] | Ratio | Budesonide solubilized [mg/ml] |
|---|---|---|---|
| 0.10 | 1.0 | 1:10 | 0.37 |
| 0.10 | 1.5 | 1:15 | 0.44 |
| 0.25 | 1.5 | 1:6 | 0.46 |
| 0.50 | 1.5 | 1:3.33 | 0.48 |
| 0.50 | 2.0 | 1:4 | 0.80 |
| 0.50 | 3.0 | 1:6 | 1.09 |

Example 11

Colloidal Solubilization of Budesonide Using Vitamin E TPGS, Polysorbate 80, and Lecithin In analogy to example 9, colloidal solutions of budesonide were prepared using both vitamin E TPGS and polysorbate 80 in combination as non-ionic surfactant component and lecithin of the commercial grade, Lipoid S 100, as phospholipid component. The other excipients and their content remained the same as in example 9.

With a vitamin E TPGS concentration of 0.04 wt.-%, a polysorbate 80 concentration of 0.06 wt.-% (equivalent to a non-ionic surfactant component concentration of 0.1 wt.-%) and a lecithin concentration of 1.0 wt.-%, it was found that budesonide could be colloidally solubilized at a concentration of 0.38 mg/ml.

With a vitamin E TPGS concentration of 0.2 wt.-%, a polysorbate 80 concentration of 0.3 wt.-% (resulting in a non-ionic surfactant component concentration of 0.5 wt.-%) and a lecithin concentration of 3.0 wt.-%, it was found that budesonide could be colloidally solubilized at a concentration of 0.95 mg/ml.

Example 12

Colloidal Solubilization of Budesonide Using macrogol-15-hydroxystearate and Lecithin In analogy to example 9, colloidal solutions of budesonide were prepared using macrogol-15-hydroxystearate as non-ionic surfactant component and lecithin of the commercial grade, Lipoid S 100, as phospholipid component. The other excipients and their content remained the same as in example 9.

With macrogol-15-hydroxystearate (commercial grade: Solutrol HS15) at a concentration ranging from 0.10 to 0.50 wt.-% and a lecithin concentration of 1.5 wt.-%, it was found that substantial amounts of budesonide could be colloidally solubilized (see table 7).

TABLE 7

| Solutrol HS 15 [wt. %] | Lipoid S100 [wt. %] | Ratio | Budesonide solubilized [mg/ml] |
|---|---|---|---|
| 0.10 | 1.5 | 1:15 | 0.43 |
| 0.25 | 1.5 | 1:6 | 0.47 |
| 0.50 | 1.5 | 1:3.33 | 0.48 |

Example 13

Colloidal Solubilization of Fluticasone Propionate Using Polysorbate 80 and Lecithin In analogy to example 9, colloidal solutions of were prepared using polysorbate 80 as non-ionic surfactant component and lecithin of the commercial grade, Lipoid S 100, as phospholipid component. However, fluticasone propionate was used instead of budesonide as poorly water soluble active agent. The other excipients and their content remained the same as in example 9.

With polysorbate 80 at a concentration of 0.10 and 0.50 wt.-% and lecithin at a concentration of 1.0 and 3.0 wt.-%, respectively, it was found that fluticasone propionate could be colloidally solubilized (see table 8), even though not to the same absolute concentration as in the case of budesonide.

TABLE 8

| Polysorbate 80 [wt. %] | Lipoid S100 [wt. %] | Ratio | Fluticasone prop. solubilized [mg/ml] |
|---|---|---|---|
| 0.10 | 1.0 | 1:10 | 0.07 |
| 0.50 | 3.0 | 1:6 | 0.18 |

Example 14

Preparation of a Sterile Colloidal Solution of Budesonide

In analogy to example 9, a sterile colloidal solution of budesonide which however contained 0.1 wt.-% polysorbate 80, 1.0 wt.-% Lipoid S100, and 300 µg/ml budesonide. Samples of this colloidal solution were analyzed using various methods. The respective properties are listed in table 9.

TABLE 9

| Property | Value |
| --- | --- |
| Mean diameter of colloidal structures | 52 nm |
| Polydispersity index | 0.28 |
| Dynamic viscosity | 1.1 mPas |
| Surface tension | 56 mN/m |
| pH | 4.4 |
| Osmolality | 278 mOsmol/kg |

The solution was further characterized by testing the nebulization performance using a PARI eFlow™ vibrating membrane nebulizer and a programmable breathing simulator. Fill volumes were 0.5 and 1.0 ml, respectively. The aerosol droplet size was analyzed using a laser diffraction test (Malvern MastersizerX) at constant flow rates of 12 (pediatric) and 20 (adult) l/min.

Furthermore, two breathing patterns representing typical adult and pediatric (3 year-old child) breathing patterns were tested. The adult pattern consisted of a tidal volume of 500 ml, 15 breaths per minute, and an inhalation/exhalation ratio of 50:50. The pediatric pattern was defined by a tidal Volume of 125 ml, 24 breaths per minute, and an inhalation/exhalation ratio of 40:60.

For the fill volume of 0.5 ml, a total aerosol output of approx. 450 mg was determined for the pediatric breathing pattern and of approx. 480 mg for the adult breathing simulation run. For the volume of 1 ml, a total aerosol output of approx. 890 mg for the pediatric breathing pattern and of approx. approx. 940 mg for the adult pattern was found. Thus, the relative output was nearly independent of the fill volume, and only marginally different for the two respective breathing patterns.

The nebulization time for the fill volume of 0.5 ml was approx. 1.1 min for both breathing patterns, and that for 1 ml was 2.1 min, again independent of the respective breathing pattern. Thus, the breathing pattern had no impact on the nebulization time, which was substantially proportional to the fill volume.

The mass median diameter of the aerosol droplets was 3.25 µm at 12 l/min, with a geometric standard deviation of 1.52. Measured at 20 l/min, the mass median diameter was 3.12 µm and the geometric standard deviation was 1.52. The total output rate was 556 mg/min for 12 l/min, and 574 mg/min for 20 l/min. The respirable aerosol fraction, defined by the aerosol droplets with a diameter of up to 5 µm, was about 84-85% in both cases. The aerosol fraction between 2 and 5 µm was approx. 72%, again without difference with regard to the flow rate. The largest fraction was that of droplets of 2 to 3 µm in diameter, which was also independent of the inhalation flow rate.

Example 15

Preparation of a Sterile Solution of Ciclesonide and Formoterol

In analogy to the composition in table 8, a sterile colloidal solution of ciclesonide containing 160 µg/ml and formoterol 20 µg/ml was prepared. After sterile filtration, no drug could be detected on the sterile-filter and 0.6 ml each were filled into V-shaped blow fill seal vials overpouched by an aluminium foil containing nitrogen.

Example 16

Preparation of a Sterile Combination Product Consisting of Budesonide and Cyclosporin A In analogy to the manufacturing process as described in the previous examples, and a sterile colloidal solution with a ratio of Budesonide:Cyclosporin=100:200 µg/ml was prepared in a mixture of 0.2% (w/w) Polysorbate 80 and 2% (w/w) Lipoid S 100). After a sterile filtration, no drug could be detected on the filter and 2.1 ml each were filled into bottle-shaped blow fill seal vials overpouched by an aluminium foil containing nitrogen.

The invention claimed is:

1. A sterile composition for administration as an aerosol, comprising a poorly water-soluble active agent, a non-ionic surfactant component, wherein the non-ionic surfactant component comprises at least one member from the group consisting of tyloxapol, polysorbates, vitamin E TPGS, and macrogol-hydroxystearates, and a phospholipid component, wherein the active agent is not a surfactant and wherein the active agent is solubilized in unilamellar liposomes.

2. The composition of claim 1, wherein the phospholipid component comprises at least one member from the group consisting of a zwitterionic phospholipid, a saturated phospholipid, a hydrogenated phospholipid, and a pure phospholipid; or a mixture of such phospholipids.

3. The composition of claim 1, wherein the weight ratio between the non-ionic surfactant component and the phospholipid component is from about 5:1 and about 1:20.

4. The composition of claim 1, further comprising one or more excipients selected from the group consisting of acids, bases, buffering agents, osmotic agents, stabilizers, antioxidants, taste-masking agents, flavors, sweetening agents, ionic surfactants, thickeners, coloring agents, fillers, and bulking agents.

5. The composition of claim 4, wherein the antioxidant is selected from the group consisting of vitamin E acetate, EDTA (di)sodium salt and a mixture thereof.

6. The composition of claim 1, wherein the composition is in the form of an aqueous liquid.

7. The composition of claim 6, wherein the average particle size of the liposomes is from about 10 nm to about 100 nm with a polydispersity index of not more than about 0.3, the composition being free of solid particles capable of sedimentation.

8. The composition of claim 6, having a non-ionic surfactant component content of about 0.01 to about 5.0 wt-%.

9. The composition of claim 6, having a phospholipid component content of 0.5 to about 5 wt.-%.

10. The composition of claim 6, wherein the aqueous liquid has a surface tension of about 30 to about 75 mN/m.

11. The composition of claim 6, wherein the aqueous liquid has a dynamic viscosity of about 0.8 to about 3.0 mPas.

12. The composition of claim 6, wherein the aqueous liquid has a pH of about 4 to about 8.

13. The composition of claim 6, wherein the aqueous liquid has an osmolality of about 200 to about 500 mOsmol/kg.

14. The composition of claim 6, wherein the composition is free of (a) cosolvents; and/or (b) a preservative.

15. The composition of claim 6, wherein the composition has a content of the poorly water-soluble active agent of between about 0.001 wt-% and about 1 wt-%.

16. The composition of claim 1, wherein the poorly water-soluble active agent is selected from the group consisting of corticosteroids, betasympathomimetics, anticholinergics, immunomodulators, anti-infectives, and cytostatics.

17. The composition of claim 1, wherein the poorly water-soluble active agent has (a) a poor taste, and/or (b) a mucosal irritation potential, and/or (c) a cough-inducing potential, and/or (d) a potential to induce bronchoconstriction.

18. The composition of claim 1, wherein the poorly water-soluble active agent is a corticosteroid and/or cyclosporine.

19. The composition of claim 18, wherein the corticosteroid is selected from the group consisting of budesonide, fluticasone, and ciclesonide; and salts of any of these corticosteroids.

20. The composition of claim 19, wherein the corticosteroid is budesonide.

21. The composition of claim 20, wherein the budesonide content is about 0.10 to about 0.5 mg/ml.

22. The composition of claim 19, wherein the corticosteroid is present in a colloidally dissolved or dispersed state.

23. The composition of claim 1, comprising a further active agent.

24. The composition of claim 23, wherein at least one of the active agent is selected from the group consisting of anti-inflammatory drugs, corticosteroids, non steroidal anti-inflammatory drugs (NSAIDs), leukotriene-antagonists, beta-sympathomimetics, anticholinergics, phosphodiesterase-inhibitors, potassium channel openers, tachykinin antagonists, kinin antagonists, IgE-synthesis inhibitors, endothelin-receptor antagonists, anesthetics, immunomodulators, antiinfectives, interferons, vasodilators, angiotensin converting enzyme (ACE) inhibitors, cytostatics, budesonide, ciclesonide, fluticasone, mometasone, beclomethasone, flunisolide; ibuprofen, ketoprofen, valdecoxib, celecoxib; zileuton, montelukast, pranlukast, roflumilast, cilomilast, zafirlukast; albuterol, formoterol, salmeterol, levalbuterol, terbutaline, pirbuterol; tiotropium, oxitropium, ipratropium; theophyllin, pentoxyphyllin, cilomast, rolipram, amrinone, cilostazol, zardaverine, benzafentrine; cromakalim, levocromakalim, pinacidil; nolpitantium, saredutant, nepadutant, osanetant; icatibant; cromoglicate, nedocromil, glucan-sulfates, suplatast, batimastat, omalizumab; lidocaine, prolocalne, mepivacaine, bupivacaine, articaine, cyclosporine, tacrolimus, sirolimus, everolimus, rapamycine, leflunomide, midostaurin, azathioprine; chloroquin, hydroxychloroquine; trimethoprim, tetracycline, doxycycline, ciprofloxacine, moxifloxacine, gatifloxacine, carbapenems, azithromycine, clarithromycine, erythromycine, ketolides, penems, aminoglycosides, tobramycin, filgrastim, pentamidine, microcidin, clerocidin; metronidazole, ketoconazole, itraconazole, voriconazole, clotrimazole, bifonazole, fluconazole, amphotericine B, natamycine, nystatine, amikacine, aciclovir, famciclovir, valaciclovir, didanosine, saquinavir, ritonavir, lamivudine, stavudine, zidovudine, ribavirin, captopril, lisinopril, perindopril, trandolapril, cilazapril, lovastatin, relaxin; suramin; sildenafil, tadalafil, vardenafil, nitrendipine, amlodipine, prostacyclins, beraprost, iloprost, bosentane, carmustine, lomustine, taxol, etoposide, cisplatin; reduced glutathione, and TNF-alpha-antibodies; and pharmaceutically acceptable salts, racemates, epimers, and of the active agents.

25. The composition of claim 24, comprising a combination of two active agents, selected from the group of combinations consisting of: (a) a corticosteroid and an immunomodulator; (b) a corticosteroid and a beta-agonist; (c) a corticosteroid and an anticholinergic agent; (d) an immunomodulator and a beta-agonist; (e) an immunomodulator and an anticholinergic agent; and (f) a beta-agonist and an anticholinergic agent.

26. The composition of claim 25, comprising a combination of two active agents, selected from the group of combinations consisting of: (a) budesonide and formoterol; (b) budesonide and tiotropium; (c) fluticasone and formoterol; (d) fluticasone and tiotropium; (e) ciclesonide and formoterol; (f) ciclesonide and tiotropium; (g) mometasone and formoterol; and (h) mometasone and tiotropium.

27. The composition of claim 1, wherein the composition is in the form of a dry solid material adapted for preparing an aqueous liquid composition.

28. A dry solid composition which is obtained by freeze-drying the composition of claim 6.

29. A medicament comprising the composition of claim 1.

30. The medicament of claim 29, being packaged in one or more single dose primary packaging means, from which it is dispensable with a dispensing variability of less than 20%, wherein the packaging means is adapted to hold a fill volume of about 0.2 ml to about 5 ml.

31. The medicament of claim 30, wherein each packaging means is a plastic container comprising a removable closure element, and wherein the container is optionally manufactured using an aseptic blow-fill-seal process design.

32. The medicament of claim 31, wherein the composition is in aqueous liquid form, and wherein the removal of the closure element yields an opening in the container of a diameter approximately corresponding to the inner or outer diameter of a male luer connection.

33. The medicament of claim 31, wherein the plastic container is designed to be, upon removal of the removable closure elements, tightly connectable to a connecting member of a nebulizer.

34. The medicament of claim 31, wherein the composition is in the form of an aqueous liquid, and wherein the plastic container comprises one or more volume or dosing marks and/or one or more imprints.

35. The medicament of claim 29, being packaged in one or more multiple dose primary packaging means which is adapted to hold a fill volume of about 2 ml to about 50 ml.

36. The medicament of claim 35, wherein the composition is in the form of an aqueous liquid, and wherein the plastic container comprises one or more volume or dosing marks and/or one or more imprints.

37. The medicament of claim 29, wherein the composition is in the form of a dry solid material.

38. The medicament of claim 37, wherein one or more single dose primary packaging means are combined with one or more further containers within one secondary package, said further containers comprising a sterile aqueous liquid for reconstituting the dry solid material to form a liquid suitable for oral or nasal inhalation.

39. Method for the manufacture of the composition of claim 1, comprising the following steps:

(a) providing the ingredients;
(b) preparing an aqueous liquid composition from the ingredients provided in step (a);
(c) sterile filtration of the composition obtained in step (b); and
(d) filling the sterile filtered composition from step (c) into sterile containers under aseptic conditions.

40. The method of claim 39, wherein at least one of the ingredients provided in step (a) is sterile.

41. The method of claim 39, wherein step (b) comprises a substep of homogenization under increased pressure, of ultrasonication and/or of heating to at least 45° C.

42. The method of claim 39, wherein the sterile containers of step (d) are plastic vials manufactured by an aseptic blow-fill-seal process.

43. The composition of claim 1, wherein the phospholipid component is selected from the group consisting of lecithin, purified and/or enriched lecithin, phosphatidylcholine fractions extracted from lecithin, dimyristoyl phosphatidylcholine (DMPC), dipalmitoyl phosphatidylcholine (DPPC) and distearoyl phosphatidylcholine (DSPC).

44. The composition of claim 6, wherein the average particle size of the liposomes is from about 10 nm to about 100 nm with a polydispersity index of not more than about 0.3, the composition being free of solid particles capable of sedimentation.

45. The composition of claim 6, having a non-ionic surfactant component content of about 0.05 to about 2.0 wt.-%.

46. The composition of claim 6, having a phospholipid component content of 0.5 to about 3 wt.-%.

47. The composition of claim 6, wherein the aqueous liquid has a surface tension of about 40 to about 70 mN/m.

48. The composition of claim 6, wherein the aqueous liquid has a dynamic viscosity of about 1.0 to about 2.0 mPas.

49. The composition of claim 6, wherein the aqueous liquid has a pH of about 4 to about 6.

50. The composition of claim 6, wherein the aqueous liquid has an osmolality of about 220 to about 350 mOsmol/kg.

51. The medicament of claim 29, being packaged in one or more single dose primary packaging means, from which it is dispensable with a dispensing variability of less than 10%, wherein the packaging means is adapted to hold a fill volume of about 0.2 ml to about 5 ml.

* * * * *

UNITED STATES PATENT AND TRADEMARK OFFICE
CERTIFICATE OF CORRECTION

| | | |
|---|---|---|
| PATENT NO. | : 7,758,886 B2 | Page 1 of 1 |
| APPLICATION NO. | : 11/106999 | |
| DATED | : July 20, 2010 | |
| INVENTOR(S) | : Jurgen Jauernig et al. | |

It is certified that error appears in the above-identified patent and that said Letters Patent is hereby corrected as shown below:

On the cover page, Item (73) please correct the name of the Assignee as follows:

Assignee: Pari Pharma GmbH, Starnberg, Germany

Signed and Sealed this

Eighth Day of November, 2011

David J. Kappos
*Director of the United States Patent and Trademark Office*